US006673250B2

(12) United States Patent
Kuennen et al.

(10) Patent No.: US 6,673,250 B2
(45) Date of Patent: Jan. 6, 2004

(54) RADIO FREQUENCY IDENTIFICATION SYSTEM FOR A FLUID TREATMENT SYSTEM

(75) Inventors: Roy W. Kuennen, Caledonia, MI (US); David W. Baarman, Fennville, MI (US); Scott A. Mollema, Grand Rapids, MI (US); Ronald C. Markham, Grand Rapids, MI (US); Terry L. Lautzenheiser, Nunica, MI (US)

(73) Assignee: Access Business Group International LLC, Ada, MI (US)

( * ) Notice: Subject to any disclaimer, the term of this patent is extended or adjusted under 35 U.S.C. 154(b) by 22 days.

(21) Appl. No.: 10/175,095

(22) Filed: Jun. 18, 2002

(65) Prior Publication Data

US 2003/0015478 A1 Jan. 23, 2003

Related U.S. Application Data

(63) Continuation-in-part of application No. 09/592,194, filed on Jun. 12, 2000, now Pat. No. 6,436,299.
(60) Provisional application No. 60/140,159, filed on Jun. 21, 1999, and provisional application No. 60/140,090, filed on Jun. 21, 1999.

(51) Int. Cl.[7] .............................. C02F 1/32; B01J 19/12
(52) U.S. Cl. ...................... 210/748; 210/85; 210/260; 210/435; 250/432 R
(58) Field of Search ................................ 210/739, 748, 210/103, 138, 143, 85, 260, 435; 250/432 R

(56) References Cited

U.S. PATENT DOCUMENTS

| 3,551,091 A | 12/1970 | Veloz |
| 3,867,661 A | 2/1975 | Waltz et al. |
| 3,923,663 A | 12/1975 | Reid |
| 4,005,330 A | 1/1977 | Glascock, Jr. et al. |
| 4,010,400 A | 3/1977 | Hollister |
| 4,017,764 A | 4/1977 | Anderson |
| 4,101,777 A | 7/1978 | Reid |
| 4,615,799 A | 10/1986 | Mortensen |
| 4,675,573 A | 6/1987 | Miram et al. |
| 4,752,401 A | 6/1988 | Bodenstein |
| 4,762,613 A | 8/1988 | Snowball |
| 4,769,131 A | 9/1988 | Noll et al. |
| 4,838,797 A | 6/1989 | Dodier |
| 4,851,818 A * | 7/1989 | Brown et al. ................ 340/603 |

(List continued on next page.)

FOREIGN PATENT DOCUMENTS

| AU | A-61741/86 | 2/1988 |
| DE | 4238388 A1 | 5/1994 |
| DE | 4421253 A1 | 3/1995 |
| EP | 0825577 A1 | 2/1998 |
| JP | 08031585 | 2/1996 |
| WO | WO 97/17761 A1 | 5/1997 |
| WO | WO 00/32298 A1 | 6/2000 |

Primary Examiner—Fred G. Prince
(74) Attorney, Agent, or Firm—Brinks Hofer Gilson & Lione

(57) ABSTRACT

A fluid treatment system is disclosed that includes a control unit that controls the overall operation of the fluid treatment system. A ballast circuit is coupled with an electromagnetic radiation emitting assembly. In the preferred fluid treatment system, the ballast circuit is inductively coupled with the electromagnetic radiation assembly. The inductively coupled ballast circuit inductively energizes an electromagnetic radiation emitting device that is located in the electromagnetic radiation emitting assembly in response to a predetermined electric signal from the control unit. In addition, the fluid treatment system includes a radio frequency identification system that is used to monitor various functional and operational aspects of the electromagnetic radiation emitting assembly and a filter assembly used in the fluid treatment system.

48 Claims, 12 Drawing Sheets

U.S. PATENT DOCUMENTS

| | | |
|---|---|---|
| 4,857,204 A | 8/1989 | Joklik |
| 4,968,437 A | 11/1990 | Noll et al. |
| 4,971,687 A | 11/1990 | Anderson |
| 5,030,889 A | 7/1991 | El-Hamamsy et al. |
| 5,041,763 A | 8/1991 | Sullivan et al. |
| 5,070,293 A | 12/1991 | Ishii et al. |
| 5,078,876 A | 1/1992 | Whittier et al. |
| 5,117,156 A | 5/1992 | Leyh et al. |
| 5,141,636 A | 8/1992 | Flanagan et al. |
| 5,230,792 A | 7/1993 | Sauska et al. |
| 5,266,215 A | 11/1993 | Engelhard |
| 5,324,423 A | 6/1994 | Markham |
| 5,328,597 A * | 7/1994 | Boldt et al. .................. 210/87 |
| 5,344,558 A | 9/1994 | Kool |
| 5,368,826 A | 11/1994 | Weltz et al. |
| 5,379,021 A | 1/1995 | Ito et al. |
| 5,381,073 A | 1/1995 | Godyak et al. |
| 5,397,963 A | 3/1995 | Manson |
| 5,404,082 A | 4/1995 | Hernandez et al. |
| 5,446,277 A | 8/1995 | Rutter |
| 5,451,791 A | 9/1995 | Mark |
| 5,506,560 A | 4/1996 | Takeuchi et al. |
| 5,529,689 A | 6/1996 | Korin |
| 5,536,395 A | 7/1996 | Kuennen et al. |
| 5,540,848 A | 7/1996 | Engelhard |
| 5,547,590 A | 8/1996 | Szabo |
| 5,573,666 A | 11/1996 | Korin |
| 5,583,402 A | 12/1996 | Moisin et al. |
| 5,594,304 A | 1/1997 | Graber |
| 5,597,482 A | 1/1997 | Melyon |
| 5,611,918 A | 3/1997 | Markham |
| 5,643,482 A | 7/1997 | Sandelman et al. |
| 5,653,877 A | 8/1997 | Mark |
| 5,660,719 A | 8/1997 | Kurtz et al. |
| 5,703,462 A | 12/1997 | Woody et al. |
| 5,779,912 A | 7/1998 | Gonzalez-Martin et al. |
| 5,817,231 A * | 10/1998 | Souza ....................... 210/96.2 |
| 5,821,632 A | 10/1998 | Normann et al. |
| 5,843,309 A | 12/1998 | Mancil |
| 5,853,572 A | 12/1998 | Krennen et al. |
| 5,856,710 A | 1/1999 | Baughman et al. |
| 5,900,178 A | 5/1999 | Johnsen |
| 5,935,431 A | 8/1999 | Korin |
| 5,949,155 A | 9/1999 | Tamura et al. |
| 5,973,455 A | 10/1999 | Mirskiy et al. |
| 6,008,593 A | 12/1999 | Ribarich |
| 6,035,266 A | 3/2000 | Williams et al. |
| 6,037,598 A | 3/2000 | Cicha |
| 6,149,801 A * | 11/2000 | Giordano et al. .............. 210/87 |
| 6,193,878 B1 * | 2/2001 | Morse et al. .................. 210/85 |
| 6,436,299 B1 * | 8/2002 | Baarman et al. ............. 210/748 |

\* cited by examiner

RADIO FREQUENCY IDENTIFICATION SYSTEM FOR A FLUID TREATMENT SYSTEM

This application claims the benefit under 35 U.S.C. §119(e) of U.S. provisional patent application Serial No.: 60/140,159 entitled Water Treatment System with an Inductively Coupled Ballast, which was filed on Jun. 21, 1999. This application also claims the benefit under 35 U.S.C. §119(e) of U.S. provisional patent application Serial No. 60/140,090 entitled Point-of-Use Water Treatment System, which was filed on Jun. 21, 1999. Further, this application is a continuation-in-part of U.S. patent application Serial No. 09/592,194 entitled Fluid Treatment System, which was filed on Jun. 12, 2000 now U.S. Pat. No. 6,436,299.

FIELD OF THE INVENTION

The present invention generally relates to a water treatment system and more particularly, to a radio frequency identification system for water treatment systems.

BACKGROUND OF THE INVENTION

The present invention addresses several problems associated with previous point-of-use home or office water treatment systems. One problem is that conventional water treatment systems, utilizing lamp assemblies with ultraviolet lamps therein, are energy-inefficient. The lamp assemblies are generally left continuously running to prevent microorganisms from reproducing within the water treatment system as a result of the ultraviolet lamp not being turned on. When a conventional lamp assembly is turned on, it takes a significant amount of start-up time before gas within the ultraviolet lamp is sufficiently excited to output light of a predetermined intensity level required to insure adequate destruction of microorganisms within the water treatment system. Water which is discharged from the water treatment system before an ultraviolet lamp is sufficiently excited may carry an unacceptably high level of live microorganisms. A continuously running lamp assembly uses a significant amount of energy and is, therefore, inefficient. Also, with the lamp assembly left running continuously, such as overnight, water residing within a water treatment system unit can become uncomfortably warm.

Another problem involves the electrical coupling of the lamp assemblies to the water treatment systems. Every time a lamp assembly is installed in or removed from a water treatment system, the lamp assembly must be mechanically and electrically coupled and uncoupled relative to the water treatment system. This often requires complicated and expensive mounting assemblies. Further, care must be taken to insure that the electrical connections are not exposed to moisture while electrical power is passing through the water treatment system.

Coaxially aligned lamp assemblies and filter assemblies are sometimes used to minimize the size of water treatment systems. A lamp assembly and filter assembly in a particular water treatment system may or may not be simultaneously removed from the water treatment system. If these assemblies are simultaneously removed, they are often very heavy as they may be filled with water and have substantial weight on their own. Alternatively, even if the lamp assembly and filter assembly are separably removable from a water treatment system, quite often problems of water spilling from one of these assemblies during handling.

Another problem faced by water treatment system units having lamp assemblies is that complicated monitoring systems are needed to monitor the lamp assemblies. As a lamp assembly ages, the intensity of light output from the lamp assembly generally diminishes. Eventually, the intensity falls below a level necessary to effect a desired microorganism-kill rate. The lamp assembly should be removed before the critical minimum intensity is reached. Accordingly, a monitor system is required to check on the light intensity within the water treatment system. These monitoring systems are typically expensive. They often require costly ultraviolet sensors with quartz windows.

Conventional ballast control circuits employ bipolar transistors and saturating transformers to drive the lamps. The ballast control circuits oscillate at frequencies related to the magnetic properties of the materials and winding arrangements of these transformers. Circuits with saturating transformer oscillators produce an output in the category of a square wave, require the transistors of the half bridge to hard-switch under load and require a separate inductor to limit the current through the discharge lamp.

These and other deficiencies in prior water treatment system units employing lamp assemblies and filter assemblies are addressed by the present invention.

SUMMARY OF THE INVENTION

The present invention discloses an electronic control system for a water treatment system that includes an inductively coupled ballast circuit. The water treatment system filters water by, amongst other things, directing a flow of water from a water supply to a filter assembly. The filter assembly removes unwanted particulates from the flow of water. After passing through the filter assembly, the water is directed to a replaceable ultraviolet lamp assembly.

The ultraviolet lamp assembly destroys organic matter in the supply of water by exposing the water to high-intensity ultraviolet light as the water flows through the ultraviolet lamp assembly. The ultraviolet lamp assembly provides virtually instantaneous high-intensity ultraviolet light at the beginning of operation, which provides advantages over prior art water treatment systems that require warm-up time. After exiting the ultraviolet lamp assembly, the flow of water is directed out of the water treatment system through an outlet assembly.

The overall operation of the water treatment system is controlled by a control unit that is electrically connected with the ultraviolet lamp assembly and the filter assembly. In the preferred embodiment, the control unit is also electrically connected with a flow sensor, an ambient temperature sensor circuit, an ambient light sensor circuit, an ultraviolet light sensor circuit, a power detection circuit, a display, an audio generation circuit, a memory storage device, a communications port and a radio frequency identification system. These devices are all monitored or controlled by the control unit and provide various benefits to the water treatment system, as will be generally set forth below.

The water treatment system further includes a memory storage device that is electrically connected with the control unit. The memory storage device is used to store various data values related to the water treatment system and its related components. In the preferred embodiment of the present invention, the memory storage device is an EEPROM or some other equivalent storage device. A communications port is connected with the control unit, which provides the ability for bi-directional communication between the control unit and a peripheral device, such as a personal computer or hand-held monitoring device.

The radio frequency identification system includes an ultraviolet light transponder that is located in each ultraviolet lamp assembly. In addition, the radio frequency identification system includes a filter transponder that is located in the filter assembly. The ultraviolet light transponder and the filter transponder communicate, using radio frequency, with the radio frequency identification system. Each transponder contains certain information that is specific to the ultraviolet lamp assembly and the filter assembly. Those skilled in the art would recognize that contact-type identification systems may be used instead of the radio frequency identification system.

In the preferred embodiment of the present invention, a fluid treatment system with a radio frequency identification system is disclosed. The fluid treatment system comprises a control unit; a base station electrically connected to the control unit; and at least one radio frequency identification transponder located in a electromagnetic radiation emitting device assembly that is in radio communication with the base station. In yet another preferred embodiment of the present invention, the electromagnetic radiation emitting assembly is replaced with a filter assembly.

Another preferred method disclosed by the present invention relates to a method of monitoring electromagnetic radiation emitting assembly information in a fluid treatment system. The method comprises the steps of providing an electromagnetic radiation emitting assembly for use in the fluid treatment system; generating an electromagnetic radiation emitting assembly information signal with an electromagnetic radiation emitting identification transponder located in the electromagnetic radiation emitting assembly; transmitting the electromagnetic radiation emitting assembly information signal to a base station located in the fluid treatment system; and directing said electromagnetic radiation emitting assembly information signal to a control unit. In another preferred embodiment, the electromagnetic radiation emitting assembly can be replaced with a filter assembly.

These and other features and advantages of the invention will become apparent upon consideration of the following detailed description of the presently preferred embodiments of the invention, viewed in conjunction with the appended drawings.

DETAILED DESCRIPTION OF THE DRAWINGS

FIG. 1 is a perspective view of a main housing of the water treatment system with its top shroud removed and a filter assembly and the ultraviolet lamp assembly removed from the base unit.

FIGS. 2A–C are exploded perspective views of major components of the water treatment system.

DETAILED DESCRIPTION OF THE PRESENTLY PREFERRED EMBODIMENT OF THE INVENTION

Figure 1:
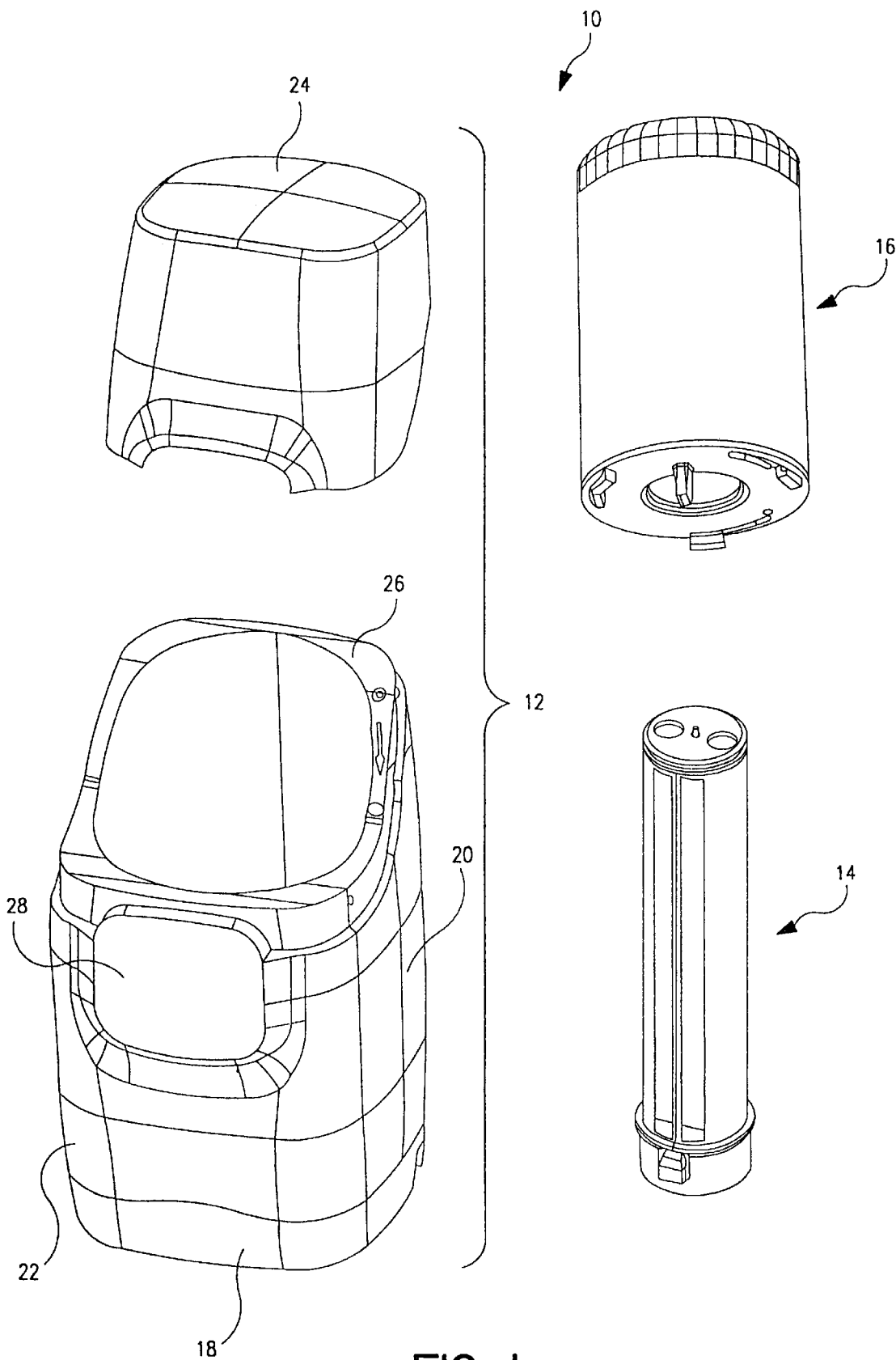

Referring to FIG. 1, the present invention discloses an electronic control system for a water treatment system 10 that generally uses carbon-based filters and ultraviolet light to purify water. In order to appreciate the present invention, it is important to have a general background of the mechanical aspects of the preferred water treatment system 10. The preferred water treatment system 10 includes a main housing 12, a replaceable ultraviolet lamp assembly 14 and a filter assembly 16. The ultraviolet lamp assembly 14 and the filter assembly 16 are removable and replaceable from the main housing 12. The main housing 12 includes a bottom shroud 18, a back shroud 20, a front shroud 22, a top shroud 24 and an inner sleeve shroud 26. A lens 28 accommodates a display 106 (see FIG. 3) so that information may be displayed about the status of the water treatment system 10 through the display 106. To assemble the water treatment system 10, the ultraviolet lamp assembly 14 is securely mounted to the main housing 12 and thereafter the filter assembly 16 is mounted over the ultraviolet lamp assembly 14 and to the main housing 12.

As those skilled in the art would recognize, the replaceable ultraviolet lamp assembly 14 may be made in such a manner that the ultraviolet lamp assembly 14 may not be replaceable. In addition, those skilled in the art would recognize that the replaceable ultraviolet lamp assembly 14 may be interchanged with several different types of electromagnetic radiation emitting assemblies. As such, the present invention should not be construed to cover only water treatment systems that use ultraviolet lamp assemblies and those skilled in the art should recognize that the disclosure of the ultraviolet lamp assembly 14 represents the preferred embodiment of the present invention.

Figure 2:
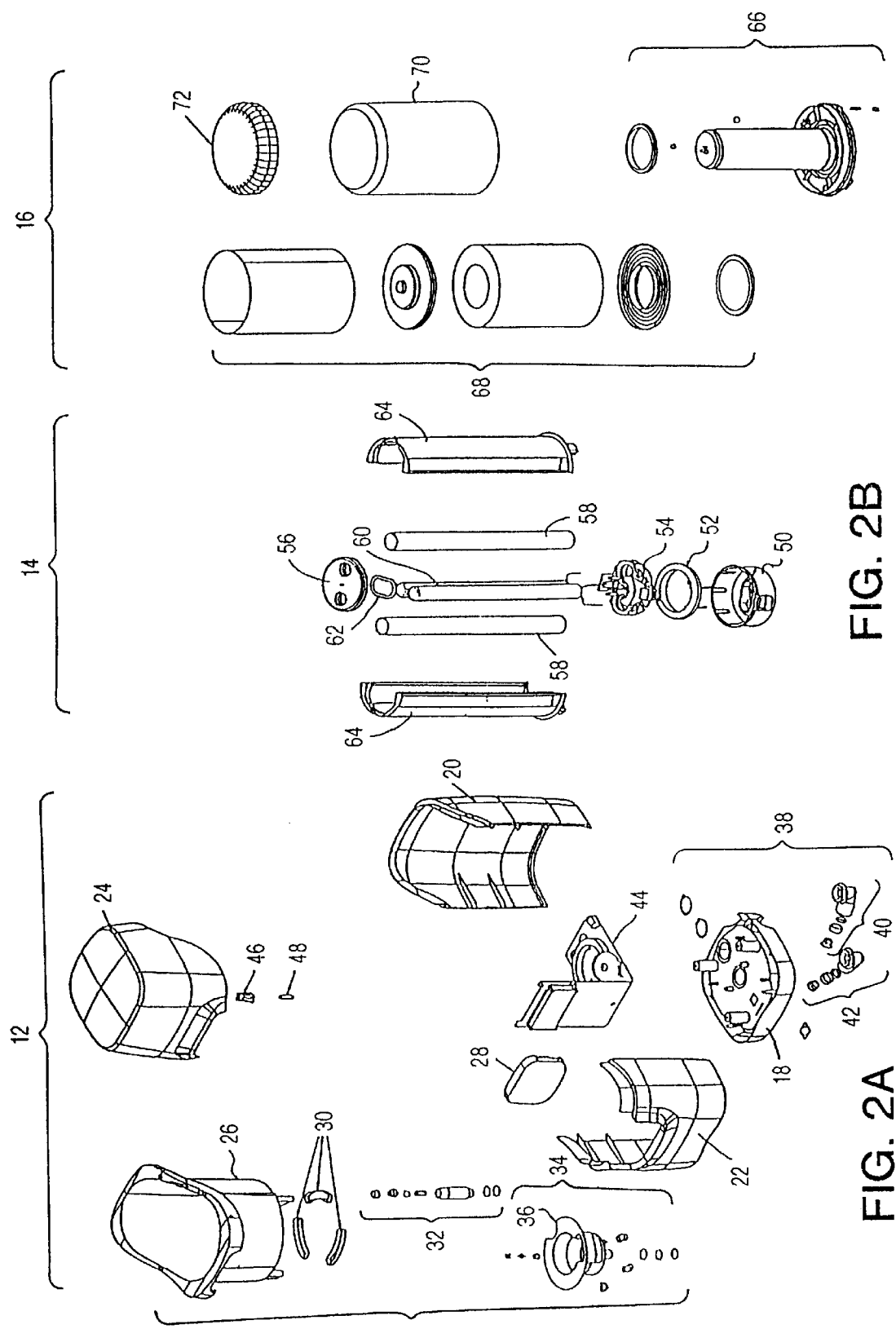

Referring to FIGS. 2A–C, the major mechanical components of the water treatment system 10 are shown in perspective view, as relevant to the present invention. As illustrated in FIG. 2A, the inner sleeve shroud 26 includes a plurality of inner sleeve covers 30, an inlet valve assembly 32 and an outlet cup assembly 34 with an outlet cup 36. A bottom shroud assembly 38 is further disclosed that includes the bottom shroud 18 along with an inlet assembly 40 and an outlet assembly 42. An electronics assembly 44 fits securely in the bottom shroud 18, the details of which will be set forth below in detail. These components are securely mounted to the bottom shroud 18, the back shroud 20, the front shroud 22, the top shroud 24, the inner sleeve shroud 26 and the lens 28 when the water treatment system 10 is fully assembled. A magnet holder 46 and a magnet 48 are also housed in the top shroud 24 in the preferred embodiment.

Referring to FIG. 2B, the ultraviolet lamp assembly 14 generally includes a base subassembly 50, a secondary coil 52, a bottom support subassembly 54, a top support assembly 56, a pair of quartz sleeves 58, an ultraviolet lamp 60, an O-ring 62 and a pair of cooperating enclosure reflector subassemblies 64. Generally speaking, the secondary coil 52, the bottom support subassembly 54 and the enclosure reflector subassemblies 64 are connected with the base subassembly 50. The enclosure reflector subassemblies 64 house the pair of quartz tubes 58, the ultraviolet lamp 60 and the O-ring 62. The top support assembly 56 fits securely over the top of the enclosure reflector assemblies 64 when the ultraviolet lamp assembly 14 is fully assembled.

As illustrated in FIG. 2C, the filter assembly 16 generally includes a base assembly 66, a filter block assembly 68, a filter housing 70 and an elastomeric filter-housing grip 72. Generally speaking, the filter block assembly 68 fits over the base assembly 66 which, in turn, is encapsulated by the filter housing 70. The filter housing grip 72 fits over the top of the filter housing 70, thereby providing a better grip for removing the filter housing 70. The filter assembly 16 filters a flow of water by directing the flow through the filter block assembly 68 before being directed to the ultraviolet lamp assembly 14.

Figure 3:
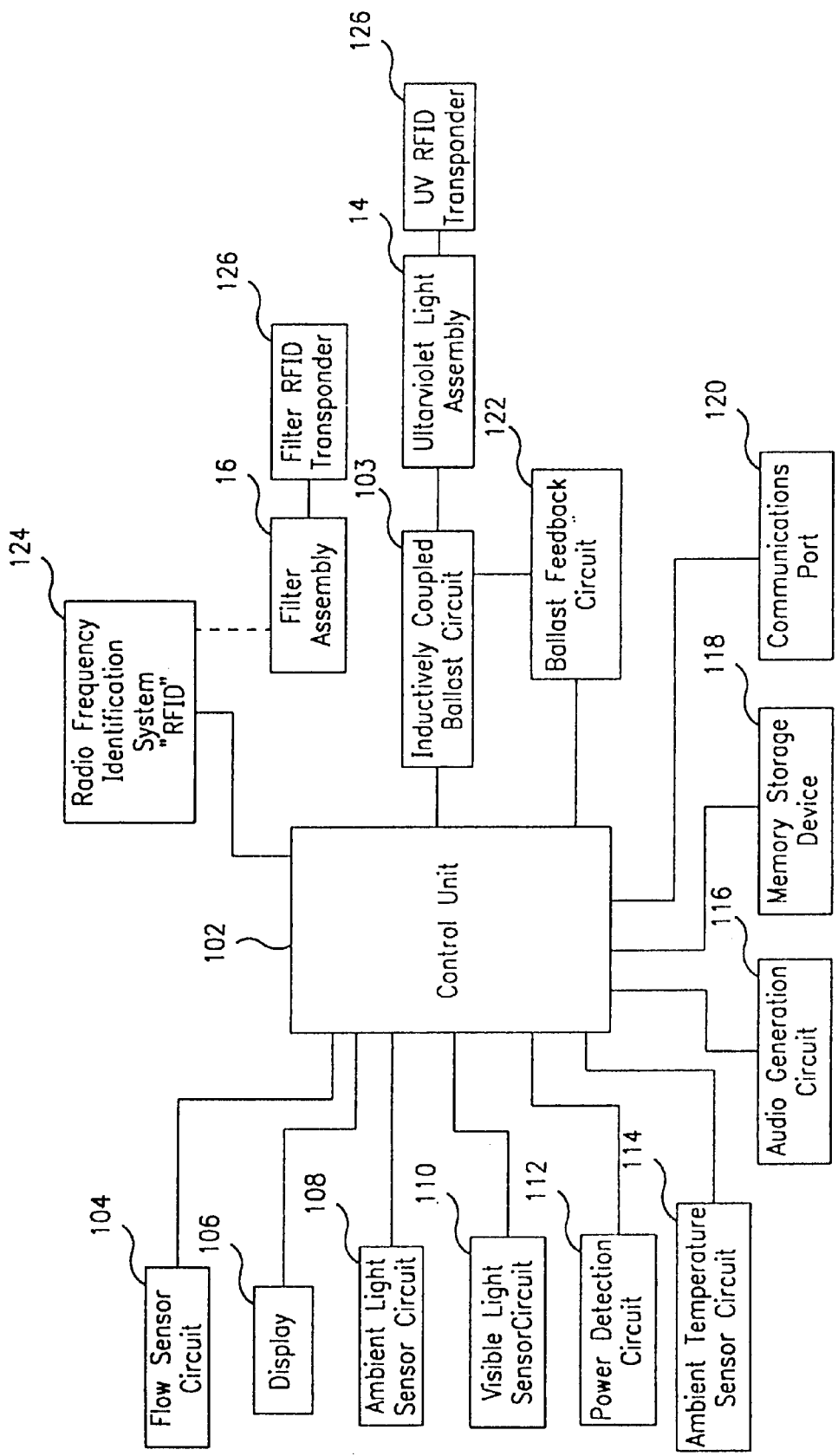
FIG. 3 depicts a block diagram of the major circuits and assemblies of the water treatment system.

Referring to FIG. 3, the present invention discloses an electronic control system 100 for the water treatment system 10 generally described above. In the preferred embodiment, the water treatment system 10 is controlled by a control unit 102, which is preferably a microprocessor. As illustrated, the control unit 102 is electrically connected with the ultraviolet lamp assembly 14 through an inductively coupled ballast circuit 103. This control unit 102 is also electrically connected to the ultraviolet lamp assembly 14 through two-way wireless communication, as will be set forth in greater detail below. During operation, the control unit 102 is capable of generating a predetermined electric signal that is directed to the inductively coupled ballast circuit, which instantaneously energizes the lamp assembly 14 which, in turn, provides high-intensity ultraviolet light that treats the flow of water.

In the preferred embodiment, the control unit 102 is also electrically connected with a flow sensor circuit 104, a display 106, an ambient light sensor circuit 108, a visible light sensor circuit 110, a power detection circuit 112, an ambient temperature sensor circuit 114, an audio generation circuit 116, a memory storage device 118, a communications port 120, a ballast feedback circuit 122 and a radio frequency identification system 124. As further illustrated in FIG. 3, an ultraviolet light radio frequency identification transponder 126 is connected with the ultraviolet lamp assembly 14 and a filter radio frequency identification transponder 128 is connected with the filter assembly 16. The ultraviolet radio frequency identification transponder 126 and the filter radio frequency identification transponder 128 communicate with the radio frequency identification system 124 using two-way wireless communication, as will be set forth in greater detail below.

Generally speaking, the flow sensor circuit 104 is used by the control unit 102 to determine when water or fluid is flowing and to keep track of the volume of water or fluid that is being processed by the water treatment system 10. The display 106 is driven by the control unit 102 and is used to display information about the status of the water treatment system 10. Several different types of displays are known in the art and may be used in the present invention; however, the preferred display is a vacuum florescent display. The ambient light sensor circuit 108 measures the amount of ambient light and, in turn, provides electrical signals to the control unit 102 so that it can adjust the intensity of the display 106 accordingly.

The visible light sensor circuit 110 provides the control unit 102 with electrical signals related to the intensity level of the light that is being emitted by the ultraviolet lamp assembly 14. This is important because these signals allow the control unit 102 to increase or decrease the intensity of the electromagnetic radiation being emitted by the ultraviolet lamp assembly 14. Those skilled in the art would recognize that the visible light sensor circuit 110 may be interchanged with various electromagnetic radiation sensor circuits that are capable of sensing the intensity of electromagnetic radiation that is emitted from various electromagnetic radiation emitting devices that may be used in the present invention.

The power detection circuit 112 provides the control unit 102 with electrical signals that indicate the presence or absence of power to the water treatment system 10. Power is provided to the water treatment system 10 from an external power source, such as a conventional power outlet. Those skilled in the art would recognize that several circuits exist that monitor external power sources and provide corresponding electrical signals in response to losses of power.

The ambient temperature sensor circuit 114 measures the ambient temperature of the atmosphere so that the water treatment system 10 can maintain a temperature level above freezing or some other predetermined temperature setting. The control unit 102 can energize the ultraviolet lamp 60 to generate heat if necessary. The audio generation circuit 116 is used by the control unit 102 to generate audible enunciations. The audible enunciations typically occur during predetermined system states that are experienced by the water treatment system 10. These predetermined system states are recognized by the control unit 102 which, in turn, activates the audio generation circuit 116 to create the audible enunciation.

As previously set forth, the memory storage device 118 is also electrically connected with the control unit 102. The memory storage device 118 is used to store various data values related to the water treatment system 10 and its related components. In the preferred embodiment of the present invention, the memory storage device 118 is an EEPROM or some other equivalent storage device. Those skilled in the art would recognize that various memory storage devices are available that could be used in the present invention.

The communications port 120 is also electrically connected with the control unit 102, which provides the water treatment system 10 with the ability to conduct bi-directional communication between the control unit 102 and a peripheral device, such as a personal computer or hand-held monitoring device. In the preferred embodiment of the present invention, the communications port 120 uses the RS-232 communication platform to communicate with the peripheral device. The communications port 120 may also be connected with the ultraviolet lamp assembly 14 and the filter assembly 16 to monitor and control various operational characteristics of these devices in other preferred embodiments. However, in the preferred embodiment of the invention, the radio frequency identification system 124 is used to report information to the control unit 102 about the ultraviolet lamp assembly 14 and the filter assembly 16.

In the preferred embodiment depicted in FIG. 3, the radio frequency identification system 124 uses signals from the ultraviolet light radio frequency identification transponder 126 and the filter radio frequency identification transponder 128 to report various information to the control unit 102. During operation, the ultraviolet light radio frequency identification transponder 126 and the filter radio frequency identification transponder 128 communicate with the radio frequency identification system 124 using wireless communication. Since the ultraviolet lamp assembly 14 and the filter assembly 16 are designed to be replaceable at the end of its useful life, each ultraviolet lamp assembly 14 and filter assembly 16 contains a transponder 126, 128 that stores information specific to each device. Those skilled in the art would recognize that the ultraviolet light radio frequency transponder could be used in conjunction with other electromagnetic radiation emitting devices or assemblies. The radio frequency identification system 124 is set forth in greater detail below.

Figure 4:
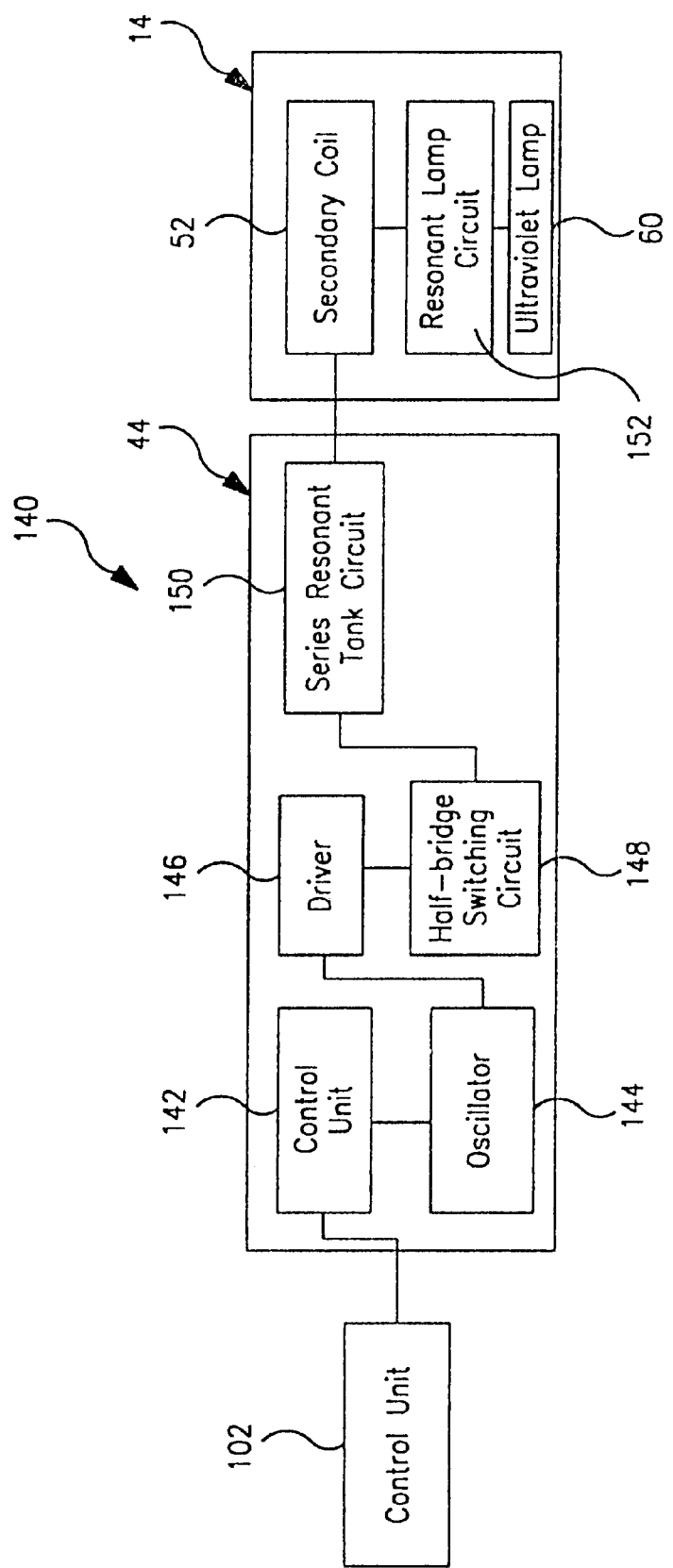
FIG. 4 depicts a block diagram of the inductively coupled ballast circuit.

Referring to FIG. 4, in the present preferred embodiment of the invention, the ultraviolet lamp assembly 14 is energized by an inductively coupled ballast circuit 103 that is electrically connected with the control unit 102. The inductively coupled ballast circuit 103 is a self-oscillating, half-bridge switching design that operates at high frequencies providing virtually instantaneous ultraviolet lamp illumination. In addition, the inductively coupled ballast circuit 103 self-oscillates once resonance is achieved, uses MOSFET transistors as switching elements, and is designed to accommodate an air-core transformer coupling arrangement, which simplifies the design of an ultraviolet lamp assembly 14. The ultraviolet lamp assembly 14 or other electromagnetic radiation emitting assemblies may be readily replaced because of the air-core transformer coupling arrangement created by the inductively coupled ballast circuit 103. Those skilled in the art would recognize that inductively coupled ballast circuit 103 can be adapted to function as a normal ballast circuit as well.

As illustrated in FIG. 4, the inductively coupled ballast circuit 103 includes a control circuit 142, an oscillator 144, a driver 146, a half-bridge switching circuit 148, a series resonant tank circuit 150, the secondary coil 52 (see FIG. 2), a resonant lamp circuit 152 and the ultraviolet lamp 60. The oscillator 144 is electrically connected with the control unit 102, which energizes the oscillator 144 by providing electric signals to the control circuit 142. During operation, the oscillator 144 provides electrical signals to the driver 146, which then causes the half-bridge switching circuit 148 to become energized. The half-bridge switching circuit 148 energizes the series resonant tank circuit 150 that, in turn, inductively energizes the ultraviolet lamp 60 in the ultraviolet lamp assembly 14.

As further illustrated in FIG. 4, the ultraviolet lamp assembly 14 houses the secondary coil 52, the resonant lamp circuit 152 and the ultraviolet lamp 60 while the electronic assembly 44 (see FIG. 2A) houses the control circuit 142, the oscillator 144, the driver 146, the half-bridge switching circuit 148 and the series resonant tank circuit 150. As previously set forth, once the series resonant tank circuit 150 is energized, the secondary coil 52 in the ultraviolet lamp assembly 14 becomes inductively energized. In the preferred embodiment, the resonant frequency for the ballast circuit 103 is about 100 kHz. As such, the secondary coil 52 in the ultraviolet lamp assembly 14 resonates at about 100 kHz as well. As previously set forth, the resonant frequency of operation can be adjusted up or down by the control unit 102 to accommodate for convenient component selection. In addition, the resonant frequency may also be controlled by the component selection in the series resonant tank circuit 150, which will be set forth in greater detail later.

Figure 5:
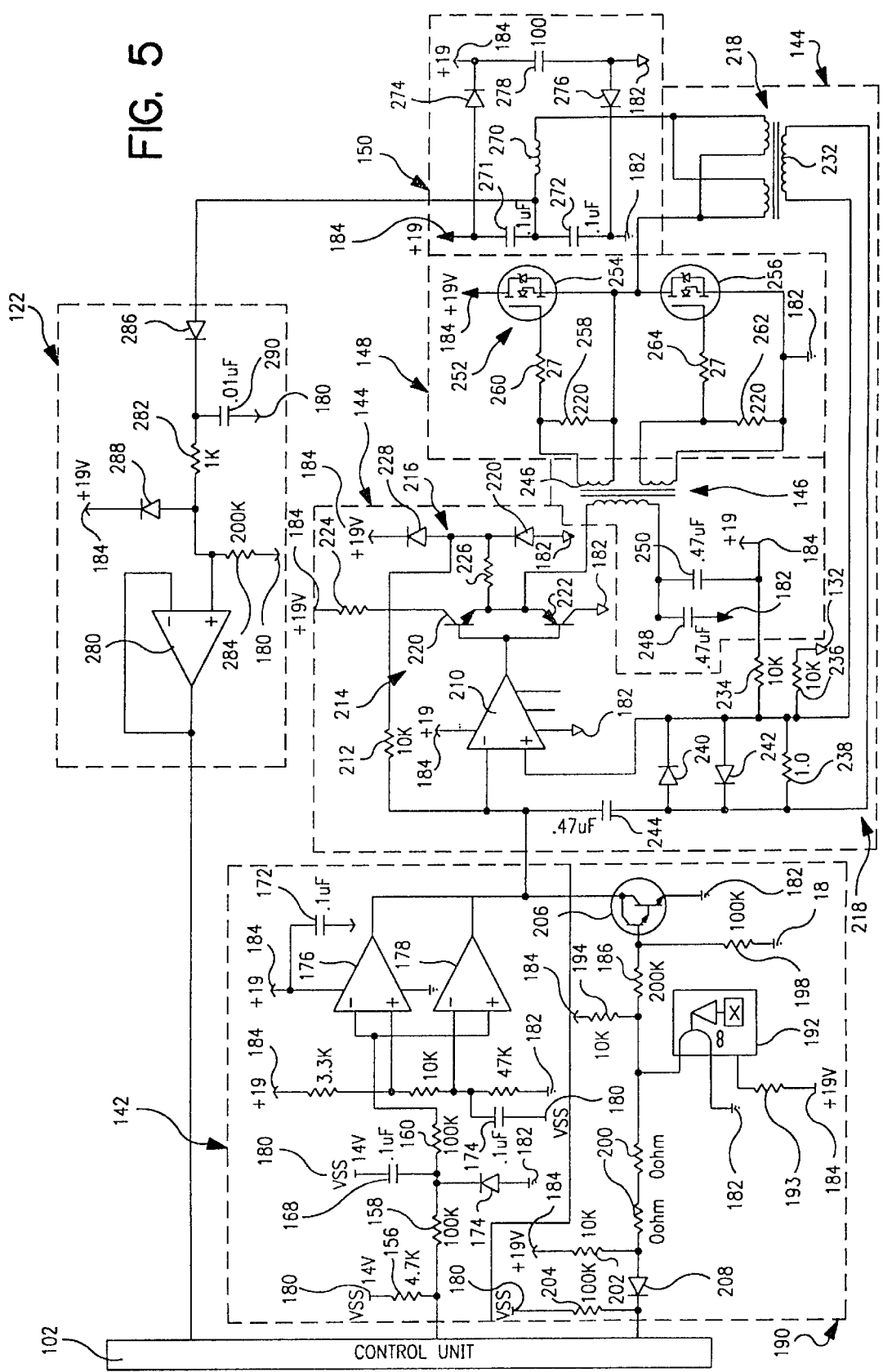
FIG. 5 is an electrical circuit schematic of a portion of the inductively coupled ballast circuit, the ballast feedback circuit and the interlock circuit.

Referring to FIG. 5, the control circuit 142 is electrically connected with the control unit 102 and the oscillator 144. The control circuit 142 includes a plurality of resistors 156, 158, 160, 162, 164, 166, a plurality of capacitors 168, 170 172, a diode 174, a first operational amplifier 176 and a second operational amplifier 178. As illustrated, resistor 156 is connected with a first direct current ("DC") power source 180, the output of the control unit 102 and resistor 158. Resistor 158 is further connected with diode 174, resistor 160 and capacitor 168. The first DC power source 180 is connected with capacitor 168, which is also connected with diode 174. Diode 174 is further connected with a ground connection 182, as those skilled in the art would recognize. Resistor 160 is connected with the negative input of operational amplifier 176 and the positive input of operational amplifier 178 to complete the current path from the control unit 102 to the operational amplifiers 176, 178.

Referring once again to the control circuit 142 depicted in FIG. 5, resistor 162 is connected with a second DC power source 184 and in series with resistors 164 and 166. Resistor 166 is connected with the ground connection 182 and capacitor 170, which is, in turn, connected with the first DC power source 180 and resistor 164. The positive input of operational amplifier 176 is electrically connected between resistors 162 and 164, which provides a DC reference voltage to operational amplifier 176 during operation. The negative input of operational amplifier 178 is electrically connected between resistors 164 and 166, which provides a DC reference voltage to operational amplifier 178 during operation. The output of operational amplifiers 176 and 178 is connected with the oscillator 144, as set forth in detail below.

During operation, the control circuit 142 receives electrical signals from the control unit 102 and, in turn, acts as a window comparator that only switches when the input voltage produced by the control unit 102 is within a certain voltage window. The preferred signal from the control unit 102 is an AC signal that, together with its duty cycle, allows the control unit 102 to turn the ultraviolet lamp 60 on and off through the remaining components of the inductively coupled ballast circuit 103, as will be set forth below. The control circuit 142 also prevents false triggering and allows positive control if the control unit 102 fails.

As illustrated in FIG. 5, the first DC power source 180 and the second DC power source 184 provide power to the circuits depicted in FIG. 5. Those skilled in the art of electronics would recognize that DC power supply circuits are well known in the art and beyond the scope of the present invention. For the purposes of the present invention, it is important to note that such circuits exist and are capable of being designed to produce various DC voltage values from a given AC or DC power source. In the preferred embodiment of the invention, a +14 VDC and a +19 VDC signal is used, as indicated throughout the figures. Those skilled in the art would recognize that the circuits disclosed in FIG. 5 could be designed to operate on different DC voltage levels and that these values should not be construed as a limitation on the present invention.

In the preferred embodiment depicted in FIG. 5, the output of the control circuit 142 is connected with an interlock circuit 190 to prevent the ultraviolet lamp 60 from becoming energized if the water treatment system 10 is not properly assembled. The interlock circuit 190 includes a magnetic interlock sensor 192, a plurality of resistors 193, 194, 196, 198, 200, 202, 204, a transistor 206 and a diode 208. Referring to FIG. 1, in the preferred embodiment of the invention, the magnetic interlock sensor 192 is positioned so that if the top shroud 24 is not securely positioned on the inner sleeve shroud 26, the water treatment system 10 will not energize the ultraviolet lamp 60. However, those skilled in the art would recognize that the magnetic interlock sensor 192 may be placed in other convenient places of the water treatment system 10 as well.

Referring to FIG. 5, the magnetic interlock circuit 190 operates by directing the output of the control circuit 142 to the ground connection 182, through transistor 206, if the magnetic interlock sensor 192 detects that the water treatment system 10 is not assembled properly, as set forth above. As those skilled in the art would recognize, if the water treatment system 10 is not assembled properly, the output of the magnetic interlock sensor 192 causes the current flowing through resistors 194, 196 and 198 to energize the gate of transistor 206, which thereby shorts the output signal of the control circuit 142 to the ground connection 182. The magnetic interlock sensor 192 is powered by the second DC power source 184 through resistor 193 and is also connected with the ground connection 182. In addition, the magnetic interlock sensor 192 sends a signal to the control unit 102, through the combination of resistors 200, 202 and 204, diode 208, first DC power source 180 and second DC power source 184. This signal also allows the control unit 102 to determine when the water treatment assembly 10 is not assembled properly. To that end, the interlock circuit 190 provides two methods of ensuring that the ultraviolet lamp 60 is not energized if the water treatment system 10 is not assembled properly.

Referring once again to FIG. 5, the oscillator 144 provides electrical signals that energize the driver 146 while the water treatment system 10 is treating a flow of water. The oscillator 144 begins operating immediately once an electrical signal is sent from the control unit 102, through control circuit 142, as set forth above. The preferred oscillator 144 comprises an operational amplifier 210, a linear bias resistor 212, a buffer circuit 214, a buffer feedback protect circuit 216 and a positive feedback circuit 218. During operation, the operational amplifier 210 receives input signals from the control circuit 142, the linear bias resistor 212 and the positive feedback circuit 218. The operational amplifier 210 is also connected with the second DC power source 184 and the ground connection 182, which energizes the operational amplifier 210.

As illustrated in FIG. 5, the preferred buffer circuit 214 comprises a first transistor 220, a second transistor 222 and a pair of resistors 224, 226. The output of operational amplifier 210 is connected with the gates of transistors 220, 222, thereby controlling operation of transistors 220, 222. The second DC power source 184 is connected with resistor 224, which is also connected with collector of transistor 220. The emitter of transistor 220 is connected with resistor 226, the emitter of transistor 222 and the input of the driver 146. The collector of transistor 222 is connected with ground connection 182. During operation, the buffer circuit 214 buffers the output signal from the operational amplifier 210 and prevents load changes from pulling the frequency of oscillation. In addition, the buffer circuit 214 increases the effective gain of the inductively coupled ballast circuit 103, which helps ensure a quick start of the oscillator 144.

The buffer feedback protect circuit 216 comprises a pair of diodes 228, 230 that are electrically connected with the output of the buffer circuit 214 by resistor 226. As illustrated in FIG. 5, the second DC power source 184 is connected with the cathode of diode 228. The anode of diode 228 and the cathode of diode 220 are connected with resistor 226 and the linear bias resistor 212. The linear bias resistor 212 provides bias feedback signals to the negative input of operational amplifier 210. In addition, the anode of diode 230 is connected with ground connection 182, which completes the buffer feedback protect circuit 216. The buffer feedback circuit 216 protects the buffer circuit 214 from drain to gate Miller-effect feedback during operation of the water treatment system 10.

As illustrated in FIG. 5, the positive feedback circuit 218 includes a first multi-winding transformer 232, a plurality of resistors 234, 236, 238, a pair of diodes 240, 242, and a capacitor 244. The secondary of the transformer 232 is electrically connected with the output of the half-bridge switching circuit 148 and the input of the series resonant tank circuit 150 as illustrated in FIG. 5. In addition, one winding from each secondary coil of the multi-winding transformer 232 is connected to another winding of the opposite secondary coil in the transformer 232.

The first primary winding of transformer 232 is electrically connected with resistors 234, 236, 238, the diodes 240, 242 and the positive input of the operational amplifier 210. The second primary winding of the transformer 232 is connected with resistor 238, the cathode of diode 242, the anode of diode 240 and capacitor 244. As such, resistor 238 and diodes 242, 244 are connected in parallel with the first and second primary windings of transformer 232, as illustrated in FIG. 5. Capacitor 244 is also electrically connected with the negative input of operational amplifier 210. In addition, resistor 234 is connected with the second DC power source 184 and resistor 236 is connected with the ground connection 182. Resistors 234, 236 and 238 protect the operational amplifier 210 from current overload and diodes 240, 242 clip the feedback signal that is sent to the input of the operational amplifier 210.

During operation, the oscillator 144 receives signals from the control circuit 142 that charges capacitor 244, which, in turn, sends an electrical signal to the negative input of the operational amplifier 210. The output of the operational amplifier 210 is electrically directed to the driver 146, which energizes the half-bridge switching circuit 148. As illustrated in FIG. 5, the transformer 232 is connected in this current path and sends electrical signals back through resistors 234, 236 and 238, which limits the current, and eventually directs the electrical signal back to the inputs of the operational amplifier 210. Transformer 232 allows the oscillator 144 to self-resonate and the inductively coupled ballast circuit 103 remains oscillating until the control unit 102 shuts the water treatment system 10 down or transistor 206 of the interlock circuit 190 pulls the input to the oscillator 144 low.

Referring once again to FIG. 5, the output of the oscillator 144 is electrically connected with the driver 146, which comprises the first primary winding of a second multi-winding transformer 246 in the preferred embodiment. The second transformer 246 is the preferred driver 146 because the phasing arrangement of the transformer 246 insures that the half-bridge switching circuit 148 will be alternately driven, which avoids shoot-through conduction. A double arrangement of capacitors 248, 250 is electrically connected with the second primary winding of transformer 246, thereby preventing DC current overflow in the transformer 246. Capacitor 246 is also connected with the ground connection 182 and capacitor 250 is also connected with the second DC power source 184.

Both secondary coils of transformer 246 are electrically connected with the half-bridge switching circuit 148, which receives energy from transformer 246 during operation. The half-bridge switching circuit 148, which is also illustrated in FIG. 5, is electrically arranged as a MOSFET totem pole half-bridge switching circuit 252 that is driven by both secondary coils of transformer 246. The MOSFET totem pole half-bridge switching circuit 252 includes a first MOSFET transistor 254 and a second MOSFET transistor 256 that provide advantages over conventional bipolar transistor switching circuits. Energy is transferred from the driver 146 to the MOSFET transistors 254, 256 through a plurality of resistors 258, 260, 262, 264. The MOSFET transistors 254, 256 are designed to soft-switch at zero current and exhibit only conduction losses during operation. The output generated by MOSFET transistors 254, 256 is more in the form of a sine wave that has fewer harmonics than that generated by traditional bipolar transistors. Using MOSFET transistors 254, 256 also provides advantages by reducing radio frequency interference that is generated by the MOSFET transistors 254, 256 while switching during operation.

In the preferred half-bridge switching circuit 148 depicted in FIG. 5, the first secondary coil of transformer 246 is connected with resistor 258 and resistor 260. The second secondary coil of transformer 246 is connected with resistor 262 and resistor 264. Resistor 260 is connected with the gate of MOSFET transistor 254 and resistor 264 is connected with the gate of MOSFET transistor 256. As illustrated, the first secondary coil of transformer 246 and resistor 258 are connected with the emitter of MOSFET transistor 254. The second secondary coil of transformer 246 and resistor 264 are connected with the gate of MOSFET transistor 256. The collector of MOSFET transistor 254 is connected with the second DC power source 184 and the emitter of MOSFET transistor 254 is connected with the collector of MOSFET transistor 256. The emitter of MOSFET transistor 256 and resistor 262 are connected with the ground connection 182.

A further benefit of the driver 146 is that multi-winding transformer 246 is a very convenient way to apply gate drive voltage to the MOSFET transistors 254, 256 that exceeds the second DC power source 184, which is a condition necessary for effective operation. The MOSFET transistors 254, 256 provide further advantages because they have diodes inherent in their design that protect the MOSFET totem pole half-bridge switching circuit 252 from load transients. In addition, over-voltages reflected from the series resonant tank circuit 150, by changes in load, are returned to supply rails by the inherent diodes within MOSFET transistors 254, 256.

Referring to FIG. 5, the output of the half-bridge switching circuit 148 is connected with the input of the series resonant tank circuit 150, which, in turn, inductively energizes the secondary coil 52 of the ultraviolet lamp assembly 14. As set forth above, in the preferred embodiment of the invention, the positive feedback circuit 218 of the oscillator 144 is connected with the output of the half-bridge switching circuit 148 and the input of the series resonant tank circuit 150 to provide feedback to operational amplifier 210 of the oscillator 144 during operation. However, the output of the half-bridge switching circuit 148 is connected with the input of the series resonant tank circuit 150 by the secondary coil of transformer 232 as illustrated in FIG. 5.

Referring to FIG. 5, the series resonant tank circuit 150 comprises an inductive coupler 270, the parallel combination of a pair of tank capacitors 271, 272, a pair of diodes 274, 276 and a capacitor 278. The inductive coupler 270 is connected with the secondary coil of transformer 232 and between tank capacitors 271, 272. Tank capacitor 271 is also connected with the second DC power source 184 and tank capacitor 272 is also connected with the ground connection 182. In addition, tank capacitor 271 and the second DC power source 184 are connected with the anode of diode 274. The cathode of diode 274 and capacitor 278 are both connected with the second DC power source 184. Capacitor 278 is connected with the anode of diode 276 and the ground connection 182. Tank capacitor 272 is also connected the cathode of diode 276.

It is important to note that the series resonant tank circuit 150 sees all of the stray inductances of the component combination of the inductively coupled ballast circuit 103. This is important because the stray inductance, which is the combined inductance seen by the series resonant tank circuit 150, will limit the power transfer dramatically to the load under any condition outside resonance. The inductance of the secondary coil 52 and the resonant lamp circuit 152 are also reflected impedance values that help determine and limit the power that is delivered to the secondary coil 52 of the ultraviolet lamp assembly. In general, brute force oscillator/transformer combinations have power transfer limits because of stray and reflected inductance. In other words, the inductance of transformers and capacitors appears in series with the load.

The frequency of operation for the series resonant tank circuit 150 is set near 100 KHz, which is determined by the inductance of the inductive coupler 270 and the parallel capacitance value of tank capacitors 271, 272, which are 0.1 uF capacitors in the preferred embodiment. Tank capacitors 271, 272 must have low dissipation factors and be able to handle high levels of current, which is about 14 amps at start up. This resonant frequency may be adjusted up or down and has been selected only for convenient component selections.

The inductive coupler 270 includes 10 turns of wire to generate the power required to inductively energize the secondary coil 52 in the ultraviolet lamp assembly 14. The inductive coupler 270 is positioned in the outlet cup 36 (see FIG. 2A) of the water treatment system 10 and wire is wrapped around the outlet cup 36 in a diameter of about 3.5 inches. In the preferred embodiment, litz wire is used for the inductive coupler 270 because litz wire is especially efficient in both performance and operating temperature, due to a fringing effect caused by the high currents that are created while operating at 100 kHz. As set forth above, the inductive coupler 270 inductively energizes the secondary coil 52 of the ultraviolet lamp assembly unit 14 during operation.

Referring to FIG. 2A, the secondary coil 52 of the ultraviolet lamp assembly unit 14 is positioned in the outlet cup 36 and the inner sleeve shroud 26 when the water treatment system 10 is assembled. In the preferred embodiment, the secondary coil 52 has 55 turns of small diameter wire that is wrapped around the secondary coil 52 in a diameter of about two inches. It is important to note that the coupling between the outlet cup 36 and the base subassembly 50, which houses the secondary coil 52, is designed to be very tolerant of gaps and misalignment. In fact, gaps are used to adjust the coupling coefficient, thereby adjusting the operating point of the ultraviolet lamp 60. In addition, the present invention provides further advantages by providing a coupling that does not require special contacts for the ultraviolet lamp assembly 14 because of the inductively coupled ballast circuit 103.

As readily apparent to those skilled in the art, the inductively coupled ballast circuit 103 set forth above may be readily incorporated into other lighting systems and provides advantages over prior art ballast circuits because it drives lamps without requiring a physical connection. This allows the ultraviolet lamp assembly 14 to be readily replaced once the ultraviolet lamp 154 has reached the end of its operational life. The inductively coupled ballast circuit 103 is capable of instantaneously energizing several different styles of lamps or bulbs.

Referring once again to FIG. 5, the ballast feedback circuit 122 is electrically connected with the inductive coupler 270 of the series resonant tank circuit 150 and the control unit 102. The ballast feedback circuit 122 provides feedback to the control unit 102 while the inductively coupled ballast circuit 103 is driving the ultraviolet lamp 60. This allows the control unit 102 to monitor the energy being provided by the inductive coupler 270 to the secondary coil 52 of the ultraviolet lamp assembly 14. This provides the control unit 102 with the ability to determine if the ultraviolet lamp 60 is on or off and also, in other embodiments, the amount of current and voltage being applied to the ultraviolet lamp 60.

As depicted in FIG. 5, the ballast feedback circuit 122 includes an operational amplifier 280, a pair of resistors 282, 284, a pair of diodes 286, 288 and a capacitor 290. The signal from the series resonant tank circuit 150 is directed to the anode of diode 286. The cathode of diode 286 is connected with capacitor 290 and resistor 282. In addition, resistor 282 is connected with the anode of diode 288, resistor 284 and the positive input of operational amplifier 280. Resistor 284 is also connected with the positive input of operational amplifier 280 and the first DC power source 180. Capacitor 290 is also connected with the first DC power source 180, while the cathode of diode 288 is connected with the second DC power source 184. The negative input of operational amplifier 280 is connected directly with the output of operational amplifier 280. The output of operational amplifier 280 is connected with the control unit 102, thereby providing the feedback signal from operational amplifier 280 to the control unit 102.

Figure 6:
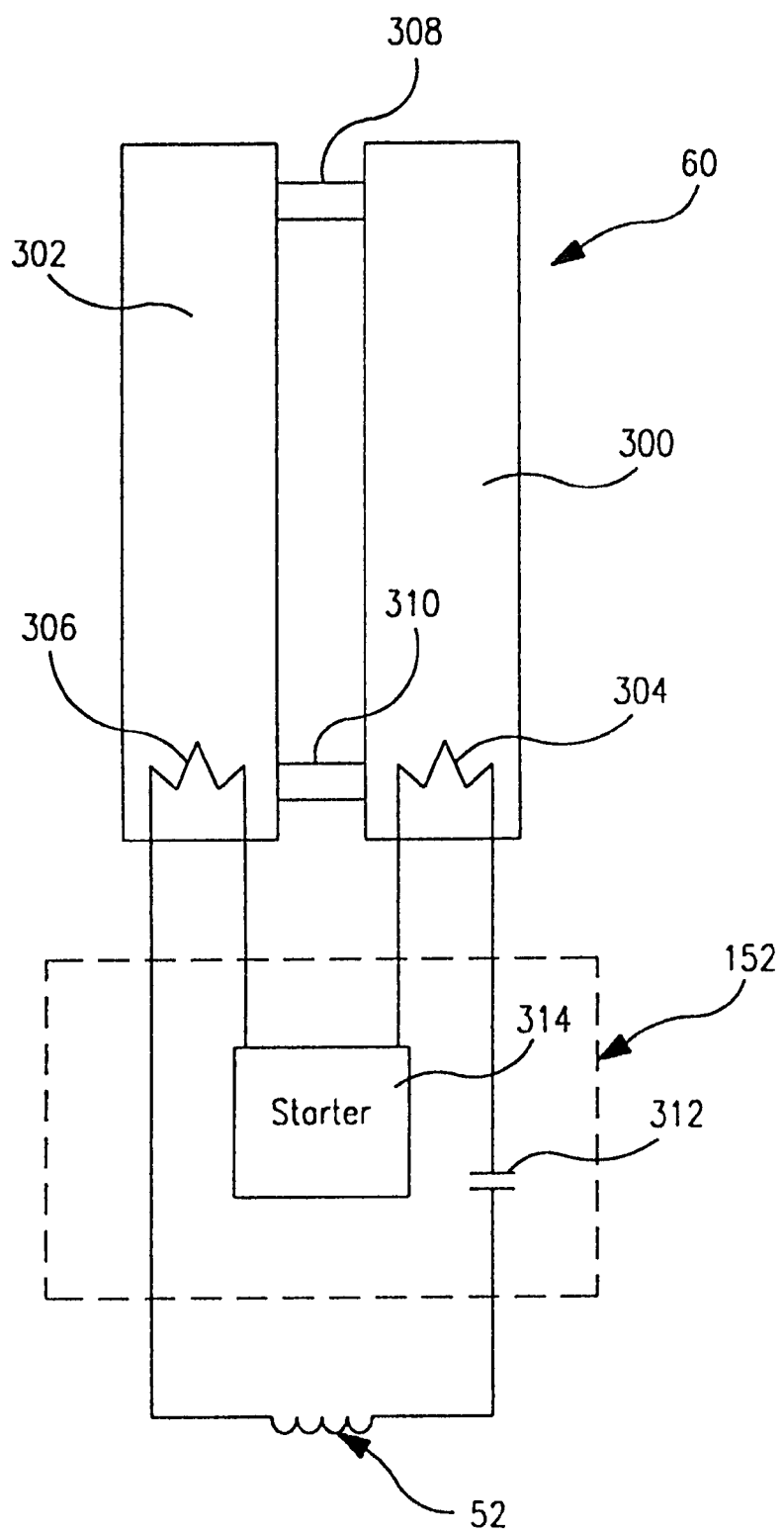
FIG. 6 depicts the secondary coil, the resonant lamp circuit and the ultraviolet lamp of the ultraviolet lamp assembly.

Referring to FIG. 6, the ultraviolet lamp assembly 14 includes the ultraviolet lamp 60, the resonant lamp circuit 152 and the secondary coil 52. The ultraviolet lamp 60 comprises a pair of bulbs 300, 302 and a pair of filaments 304, 306. The bulbs 300, 302 are held together with an upper connection bracket 308 and a lower connection bracket 310. The secondary coil 52 is connected with the resonant lamp circuit 152, which, in turn, is connected with the filaments 304, 306 of the ultraviolet lamp 60. The resonant lamp circuit 152 comprises a capacitor 312 that is electrically connected with a starter circuit 314.

Although an ultraviolet lamp assembly 14 is set forth in the preferred embodiment of the present invention, as previously set forth, those skilled in the art would recognize that other electromagnetic radiation emitting assemblies may be used in the present invention. For example, the ultraviolet lamp assembly 14 may use a pulsed white light lamp or a dielectric barrier discharge lamp to deactivate microorganisms in the flow of water. Those skilled in the art would recognize that the inductively coupled ballast circuit 103 may be used to drive various types of electromagnetic radiation emitting devices that could be used in the present invention. As such, the present invention should not be construed to only cover water treatment systems that use an ultraviolet lamp assembly 14 that includes ultraviolet lamps 300.

Figure 7:
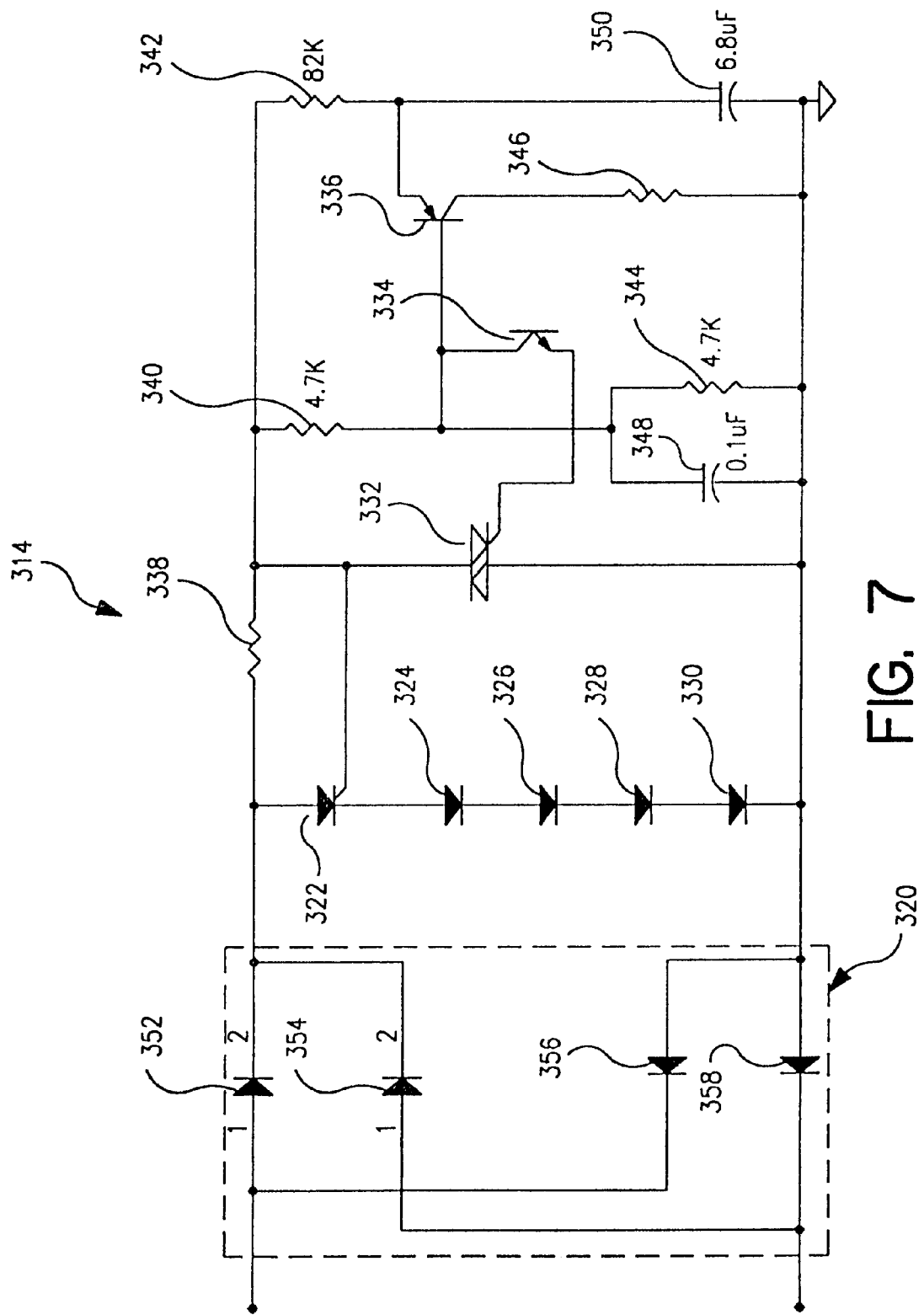
FIG. 7 is an electrical circuit schematic of the starter circuit.

As illustrated in FIG. 7, the starter circuit 314 comprises a bridge rectifier circuit 320, a silicon-controlled rectifier 322, a series arrangement of diodes 324, 326, 328, 330, a triac 332, a plurality of transistors 334, 336, a plurality of resistors 338, 340, 342, 344, 346 and a plurality of capacitors 348, 350. As those skilled in the art would recognize, the triac 332 may be any equivalent device, such as a FET transistor or a silicon controlled rectifier. In addition, those skilled in the art would recognize that the bridge rectifier circuit 320 comprises a plurality of diodes 352, 354, 356, 358 that are connected with the filaments 304, 306 of the ultraviolet lamp 60.

Referring to FIG. 7, the bridge rectifier circuit 320 is connected with silicon-controlled rectifier 322, resistor 338 and the ground connection 182. Silicon-controlled rectifier 322 is also connected with the series arrangement of diodes 324, 326, 328, 330 and the triac 332, which are both also connected with the ground connector 182. Resistor 338 is connected with triac 332, resistor 340 and resistor 342. Resistor 340 is connected with the collector of transistor 334, the gate of transistor 336, capacitor 348 and resistor 344. Capacitor 348 and resistor 344 are further connected with the ground connection 182. Resistor 342 is connected with the emitter of transistor 336 and capacitor 350, which is also connected with the ground connection 182. Triac 332 is connected with the emitter of transistor 334, and the gate of transistor 334 is connected with the collector of transistor 336 and resistor 346. Resistor 346 is connected with the ground connection 182 to complete the starter circuit 314.

Referring back to FIG. 6, during operation, capacitor 312 changes and limits the current supplied to the ultraviolet lamp 60 from the secondary coil 52 by changing the reflected impedance of the ultraviolet lamp 60 through the inductive coupler 270 (see FIG. 5) of the series resonant tank circuit 150. The starter circuit 314 is designed to short filaments 304, 306 during start-up, thereby causing maximum preheat of the bulbs 300, 302. This allows the ultraviolet lamp 60 to strike maximum dispersion of the mercury in bulbs 300, 302, thereby causing maximum intensity and delivering the highest dose of ultraviolet light to the water as it passes through the ultraviolet lamp assembly 14. In other words, the starter circuit 314 is designed so that the ultraviolet lamp 60 instantly turns on at maximum intensity. The placement of mercury in bulbs 300, 302 is important for maximum output. When the mercury condenses within the plasma path, the mercury is dispensed more evenly throughout bulbs 300, 302. The faster dispersion also allows quicker peak intensity, thereby providing the ability to give the flow of water a faster, more intense dose of ultraviolet light at start-up.

Referring to FIG. 2B, the O-ring 62 acts as a heat sink and is purposefully placed between the path of water, which flows through the pair of quartz tubes 58, and the ultraviolet lamp 60 plasma path to allow the mercury to condense within the plasma path for improved instant ultraviolet light output. As the ultraviolet lamp 60 is energized, the full-circuit voltage potential is applied across capacitor 312, filaments 304, 306 and the starter circuit 314. Because of the low impedance value of the filaments 304, 306 and the starter circuit 314, which acts as a short at start-up, the current is high for maximum preheat of the ultraviolet lamp 60. This causes the preheat of the ultraviolet lamp 60 to disperse some initial mercury at start-up. When the starter circuit 314 heats up, the starter circuit 314 RC time constant releases the shorting device, which is the triac 332 in the preferred embodiment, thereby providing full voltage across the filaments 304, 306. The starter circuit 314 allows a better start than a thermister because thermisters consume more energy after opening and do not open as quickly.

Figure 8:
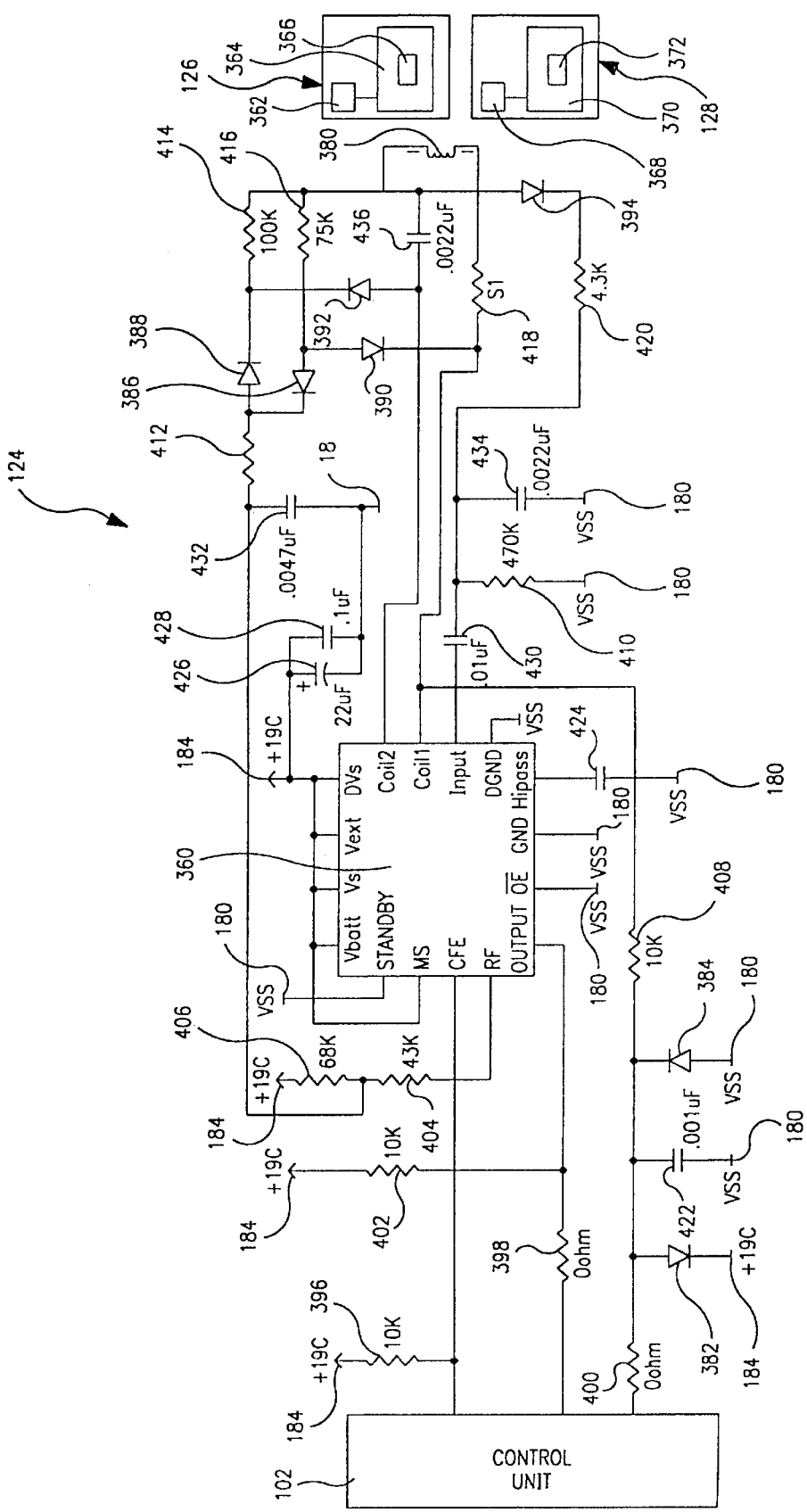
FIG. 8 illustrates an electrical circuit schematic of the radio frequency identification system used in the water treatment system

Referring to FIG. 8, the preferred radio frequency identification system 124 is illustrated electrically connected with the control unit 102. The radio frequency identification system 124 uses a base station to communicate with the ultraviolet light radio frequency identification transponder 126 and the filter radio frequency identification transponder 128. The radio frequency identification system 124 allows contactless reading and writing of data, which is transmitted bidirectionally between the base station 360 and the transponders 126, 128. In the preferred embodiment, the radio frequency identification system 124 is manufactured by TEMIC Semiconductors under model number TR5551A-PP.

The radio frequency identification system 124 is used by the control unit 102 to keep track of information specific to each ultraviolet lamp assembly 14 and filter assembly 16. As previously set forth, the ultraviolet lamp assembly 14 and the filter assembly 16 are both designed to be readily replaceable. Since the ultraviolet light radio frequency identification transponder 126 and the filter radio frequency transponder 128 are located in the ultraviolet lamp assembly 14 or the filter assembly 16, these devices are never separated, which allows the control unit 102 to read and write information to and from the transponders 126, 128 through the base station 360.

Referring once again to FIG. 8, the ultraviolet light radio frequency identification transponder 126 includes a transponder antenna 362 and a read/write IDIC® (e5551) chip 364. The read/write IDIC® (e5551) chip further includes an EEPROM device 366 that physically stores the relevant information for each respective ultraviolet lamp assembly 14 in memory locations. In the presently preferred embodiment, the information consists of an ultraviolet lamp serial number, ultraviolet lamp start limit, ultraviolet lamp on-time limit, ultraviolet lamp install time limit, ultraviolet lamp cycle on-time, cycle mode low temperature, minimum ultraviolet lamp on-time, ultraviolet lamp high-mode time and ultraviolet lamp preheat time. In addition, the EEPROM device 366 in the ultraviolet light radio frequency identification transponder 126 allows the control unit 102 to keep track of ultraviolet lamp install time, ultraviolet lamp powered time, ultraviolet lamp starts and total ultraviolet lamp cold starts.

The ultraviolet lamp serial number is unique to each ultraviolet lamp assembly 14 and allows the control unit 102 of the water treatment system 10 to keep track of which ultraviolet lamp assemblies 14 have been installed in the water treatment system 10. The ultraviolet lamp start limit relates to the maximum allowed number of ultraviolet lamp starts and the ultraviolet lamp on-time limit relates to the maximum allowed installation time for the ultraviolet lamp 60. The ultraviolet lamp install time limit relates to the maximum allowable installation time for the ultraviolet lamp assembly 14 and the ultraviolet lamp cycle on-time relates to the minimum amount of time the ultraviolet lamp 60 needs to be energized in low-temperature mode. The cycle mode low-temperature information relates to the temperature value to which the water treatment system 10 switches to low-temperature mode and the minimum ultraviolet lamp on-time relates to the minimum amount of time the ultraviolet lamp 60 must remain energized. The ultraviolet lamp high-mode time information relates to the amount of time the ultraviolet lamp 60 operates in high mode and the ultraviolet lamp preheat time relates to the amount of time the ultraviolet lamp 60 needs to be preheated.

As previously set forth, the EEPROM device 366 in the ultraviolet light radio frequency identification transponder 126 is also capable of keeping track of the ultraviolet lamp install time. This information tracks the number of hours that the current ultraviolet lamp 60 has been plugged into the water treatment system 10. In the preferred embodiment, for every minute the ultraviolet lamp 60 is plugged into the water treatment system 10, one minute is added to the total. The EEPROM device 366 also keeps track of the ultraviolet lamp powered time and the total ultraviolet lamp powered time. The ultraviolet lamp powered time and the total ultraviolet lamp powered time keeps track of the amount of time the ultraviolet lamp 60 has been on so that the control unit 102 can determine if a new ultraviolet lamp assembly 14 needs installed. The ultraviolet lamp starts memory location stores the number of times the ultraviolet lamp 60 has been started, so that the control unit 102 can use this information to determine the end of life of the ultraviolet lamp 60. The total ultraviolet lamp cold-starts memory location tracks the number of times the ultraviolet lamp 60 has been started when the ambient temperature sensor 114 indicates that the temperature is below a predetermined threshold value.

Referring once again to FIG. 8, the filter radio frequency identification transponder 128 includes a transponder antenna 368 and a read/write IDIC® (e5551) chip 370. The read/write IDIC® (e5551) chip 370 further includes an EEPROM device 372 that physically stores the relevant information for each respective filter assembly 16 in memory locations. In the present preferred embodiment, the relevant information consists of a filter assembly serial number, a filter assembly volume limit, a filter assembly install time limit, and a plugged filter assembly threshold percent.

The filter assembly serial number is used for unique identification of different filter assemblies 16 so that the control unit 102 can monitor which filter assemblies 16 have been installed in the water treatment system 10. The filter assembly volume limit is associated with the volume of water the filter assembly is designed to filter before reaching the end of its useful life. The filter assembly install time limit is used by the control unit 102 to compute the remaining life of the filter assembly 16 based on a predetermined allowable wet time. The plugged filter assembly threshold percent contains the maximum allowable percentage of flow reduction for the filter assembly 16 before it needs replaced. This maintains the percent of degradation of the filter assembly 16 before a plugged filter assembly 16 error is initiated by the control unit 102.

The radio frequency identification system 124 includes the base station 360, a coil 380, a plurality of diodes 382, 384, 386, 388, 390, 392, 394, a plurality of resistors 396, 398, 400, 402, 404, 406, 408, 410, 412, 414, 416, 418, 420 and a plurality of capacitors 422, 424, 426, 428, 430, 432, 434, 436 that are electrically connected as illustrated in FIG. 8. Those skilled in the art would recognize that the connection of the aforementioned components is well known to those skilled in the art. The radio frequency identification system 124 has been installed in the water treatment system 10 using specifications set forth for the TK5551A-PP, which, as previously set forth, is manufactured by TEMIC Semiconductors. For the purpose of the present invention, it is important to note that the base station 360 uses the coil 380 for bidirectional communication with the ultraviolet light radio frequency identification transponder 126 and the filter radio frequency identification transponder 128.

The control unit 102 is electrically connected with the base station 360 so that the control unit 102 can communicate with the base station 360. As such, the control unit 102 is capable of reading and writing information to and from the ultraviolet light radio frequency identification transponder 126 and the filter radio frequency identification transponder 128 through the base station 360 by using the coil 380. The radio frequency identification system 124 is connected with the first DC power source 180 and the second DC power source 184 as illustrated in FIG. 8, which provides the radio frequency identification system 124 with energy to function during operation.

In the preferred embodiment, a life message that relates to the ultraviolet lamp assembly 14 and the filter assembly 16 is displayed on the display 106 of the water treatment system 10. This allows users of the water treatment system 10 to visibly be notified of the status of both the ultraviolet lamp assembly 14 and the filter assembly 16. One of the main uses of the radio frequency identification system 124 is to provide and afford product compatibility with future design changes in the ultraviolet lamp assembly 14 and filter assembly 16.

The radio frequency identification system 124 allows the control unit 102 to know how interface with the ultraviolet lamp assembly 14 and filter assembly 16. The control unit 102 not only monitors the life of the ultraviolet lamp assembly 14 and filter assembly 16, but it also uses data in the replacement ultraviolet lamp assemblies 14 and filter assemblies 16 to calculate this data. The radio frequency identification system 124 also imports additional information that allows the control unit 102 to adjust to specific parameters that may change in future systems. When the water treatment system 10 provides for preheat time of the ultraviolet lamp assembly 14, UV sensor thresholds and plug flow volumes of the filter assembly 16 the radio frequency identification system 124 allows the control unit 102 to import the latest changes in these parameters and perform accordingly.

The control unit 102 imports this data from the ultraviolet lamp assembly 14 and filter assembly 16 and then stores this data until the next replacement is installed in the water treatment system 10. This allows the data imported to be specific to a lamp batch or type. The filter assembly 16 has plug data that allows the control unit 102 to import this data and know when the filter assembly 16 is starting to plug. This is also specific to filter pressure and flow controls of the water treatment system 10.

The control unit 102 also transfers user data to replacement ultraviolet lamp assemblies 14 and filter assemblies 16 to inform the devices of user habits. The control unit 102 can store user habit information in respective ultraviolet lamp assemblies 14 and filter assemblies 16 for gathering at a later date. The radio frequency identification system 124 can also be used to transfer password information to and from the ultraviolet lamp assembly 14 and filter assembly 16 as well as a wake up sequence to request each unit to independently become active.

Those skilled in the art would recognize that other identification systems could be used with the present invention, such as contact-type identification systems. However, the present preferred embodiment of the invention uses a radio frequency identification system 124 because of the inherent benefits such a system provides.

Figure 9:
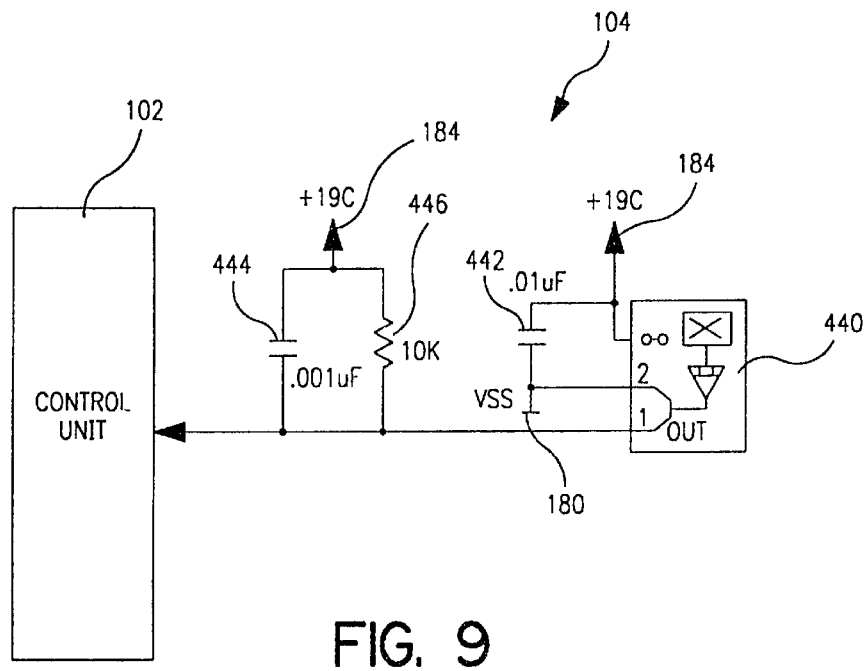
FIG. 9 is an electrical circuit schematic of the flow sensor circuit.

Referring to FIG. 9, the flow sensor circuit 104 is connected with the control unit 102 to provide electrical signals to the control unit 102 indicating that water is flowing through the water treatment system 10. The flow sensor circuit 104 includes a flow sensor 440, a plurality of capacitors 442, 444 and a resistor 446. The flow sensor is manufactured by Allegro under model number 3134. Capacitor 442 is connected with the flow sensor 440, the first DC power source 180 and the second DC power source 184. The output of the flow sensor 440 is connected with the parallel combination of resistor 446 and capacitor 444, before being connected with the control unit 102. Resistor 446 and capacitor 444 are also connected with the second DC power source 184. During operation, the flow sensor 440 delivers electrical signals to the control unit 102, which indicates that water is flowing in the water treatment system 10, thereby causing the control unit 102 to instantaneously energize the ultraviolet lamp 60. Those skilled in the art would recognize that several variations exist on the disclosed flow sensor circuit 104 and that the disclosed flow sensor circuit 104 is provided by way of example only and should be not construed as a limitation of the present invention.

Figure 10:
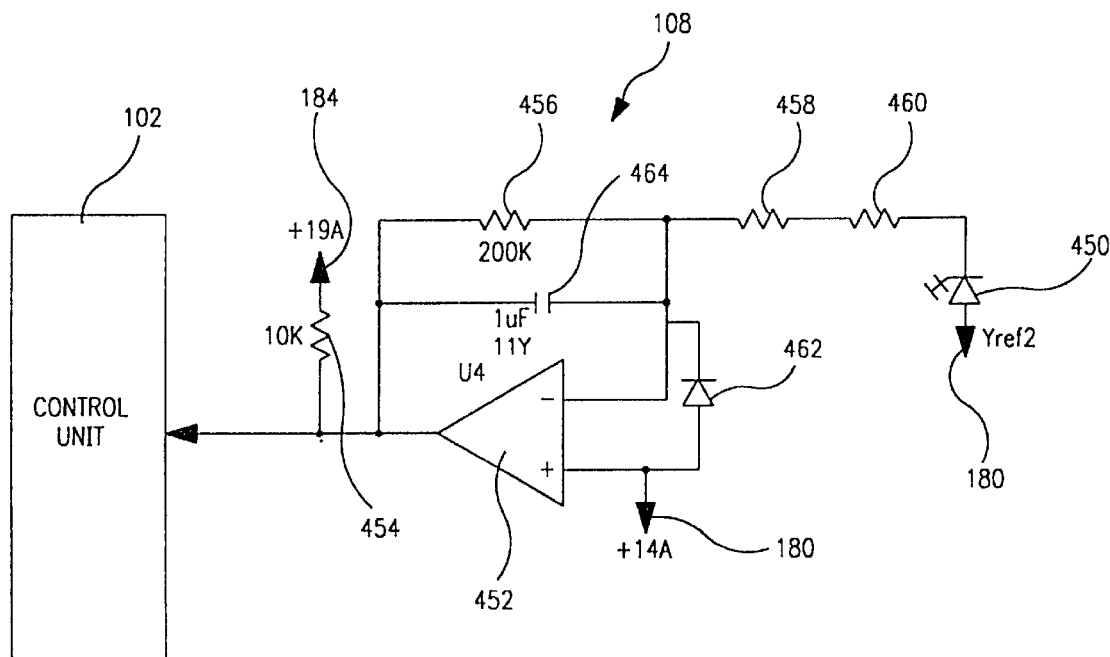
FIG. 10 is an electrical circuit schematic of the ambient light sensor circuit.

Referring to FIG. 10, the ambient light sensor circuit 108 comprises a photosensitive diode 450, an operational amplifier 452, a plurality of resistors 454, 456, 458, 460, a diode 462 and a capacitor 464 electrically connected as illustrated. For purposes of the present invention, it is sufficient to note that the photosensitive diode 450 provides electrical signals to the negative input of the operational amplifier 452, which, in turn, conditions the signal for the control unit 102. The ambient light sensor circuit 108 is powered by the first DC power source 180 and the second DC power source 184. 10. Those skilled in the art would recognize that several variations exist on the design of ambient light sensor circuits 108 and that the presently disclosed preferred embodiment should not be construed as a limitation on the present invention.

Figure 11:
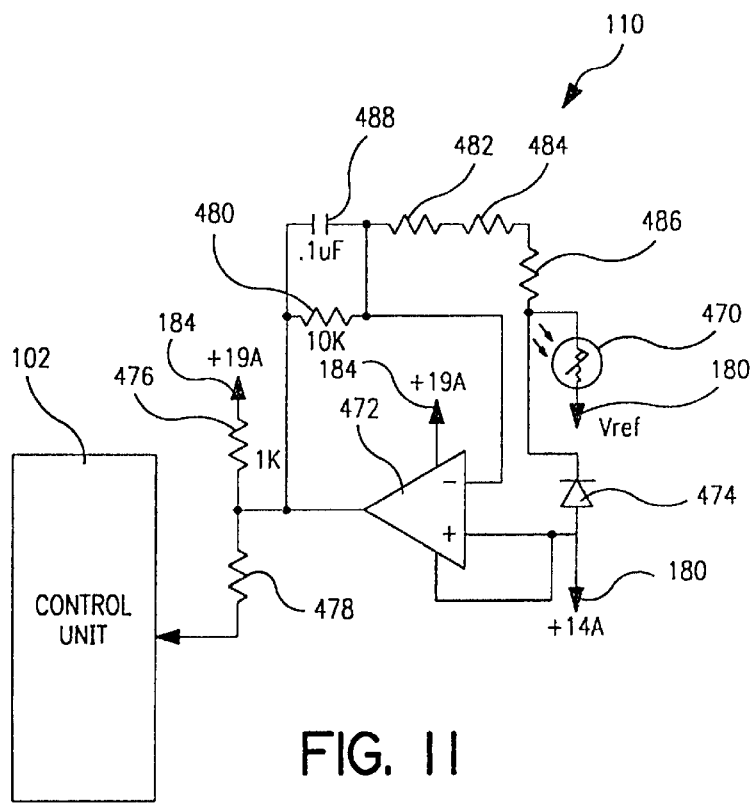
FIG. 11 is an electrical circuit schematic of the ultraviolet light sensor circuit.

Referring to FIG. 11, as previously set forth, the visible light sensor circuit 110 is connected with the control unit 102 to provide electrical signals to the control unit 102 corresponding to the intensity of the ultraviolet lamp 60 during operation. In the preferred embodiment, the visible light sensor circuit 110 comprises a photosensitive resistor 470, an operational amplifier 472, a diode 474, a plurality of resistors 476, 478, 480, 482, 484, 486 and a capacitor 488 electrically connected as depicted in FIG. 11. In addition, the visible light sensor circuit 110 is powered by the first DC power source 180 and the second DC power source 184. Those skilled in the art would recognize that the visible light sensor circuit 110 takes the electrical signal generated by the photosensitive resistor 470 and amplifies it with the operational amplifier 472, before being directed to the control unit 102. Further, those skilled in the art would recognize that the design of visible light sensor circuits 110 can vary and that the disclosed ultraviolet light sensor circuit 110 is by way of example only and should not be construed as a limitation of the present invention.

Figure 12:
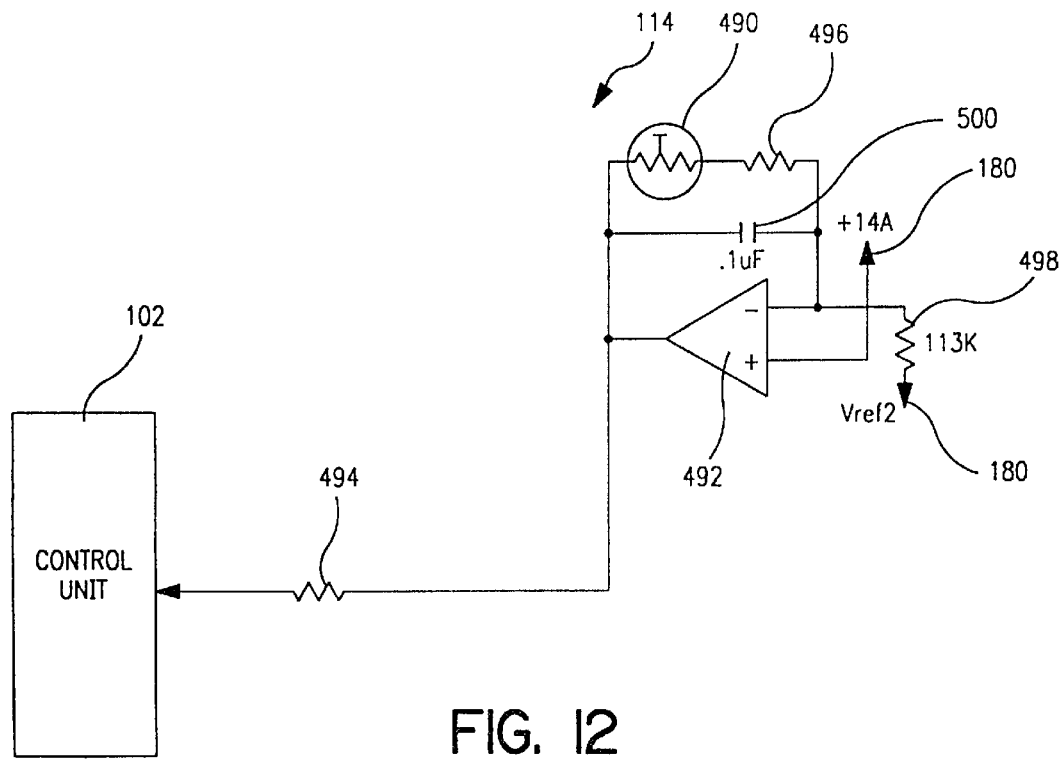
FIG. 12 is an electrical circuit schematic of the ambient temperature sensor circuit.

Referring to FIG. 12, as previously set forth, the preferred ambient temperature sensor circuit 114 is connected with the control unit 102 to provide the control unit 102 with electrical signals that change with corresponding changes in the ambient temperature. The ambient temperature sensor circuit 114 comprises a thermistor 490, an operational amplifier 492, a plurality of resistors 494, 496, 498 and a capacitor 500 that are electrically connected as illustrated in FIG. 12. During operation, the voltage drop across thermistor 490 changes as the ambient temperature changes, thereby causing the electrical signal that is sent from the output of the operational amplifier 492 to the control unit 102 to either increase or decrease. Those skilled in the art would recognize that the design of ambient temperature sensor circuits 114 can vary. The preferred ambient temperature sensor circuit 114 illustrated in FIG. 12 is by way of example only and should not be construed as a limitation of the present invention.

Figure 13:
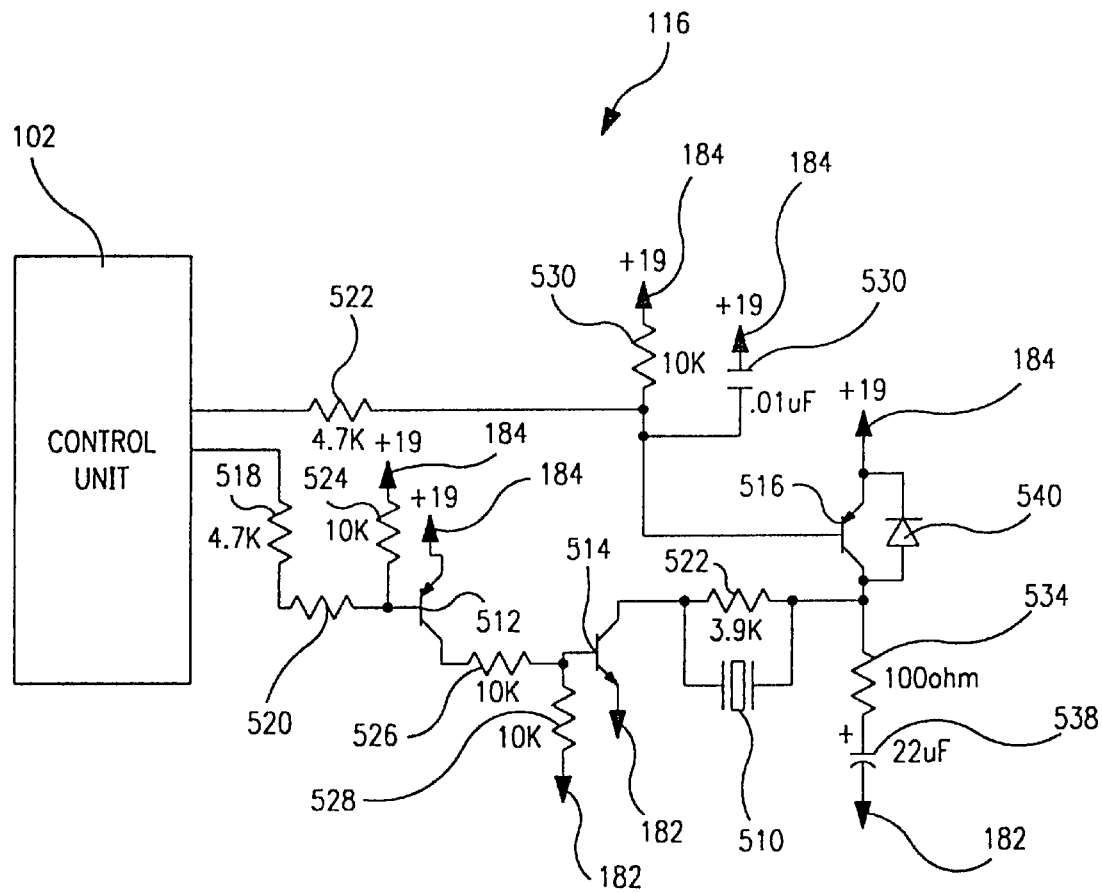
FIG. 13 is an electrical circuit schematic of the audible generation circuit.

Referring to FIG. 13, as previously set forth, the preferred audio generation circuit 116 is connected with the control unit 102 for generating audible enunciations in response to predetermined system states. The preferred audio generation circuit 116 comprises a piezoelectric element 510, a plurality of transistors 512, 514, 516, a plurality of resistors 518, 520, 522, 524, 526, 528, 530, 532, 534, a plurality of capacitors 536, 538 and a diode 540, which are electrically connected as depicted in FIG. 13. As readily apparent to those skilled in the art, the control unit 102 is capable of energizing the piezoelectric element 510, thereby causing the piezoelectric element 510 to generate audible tones through vibrations. Those skilled in the art would recognize that several devices and circuits exist that are capable of generating audible tones. The presently disclosed audio generation circuit 116 is by way of example only and likewise should not be construed as a limitation of the present invention.

Figure 14:
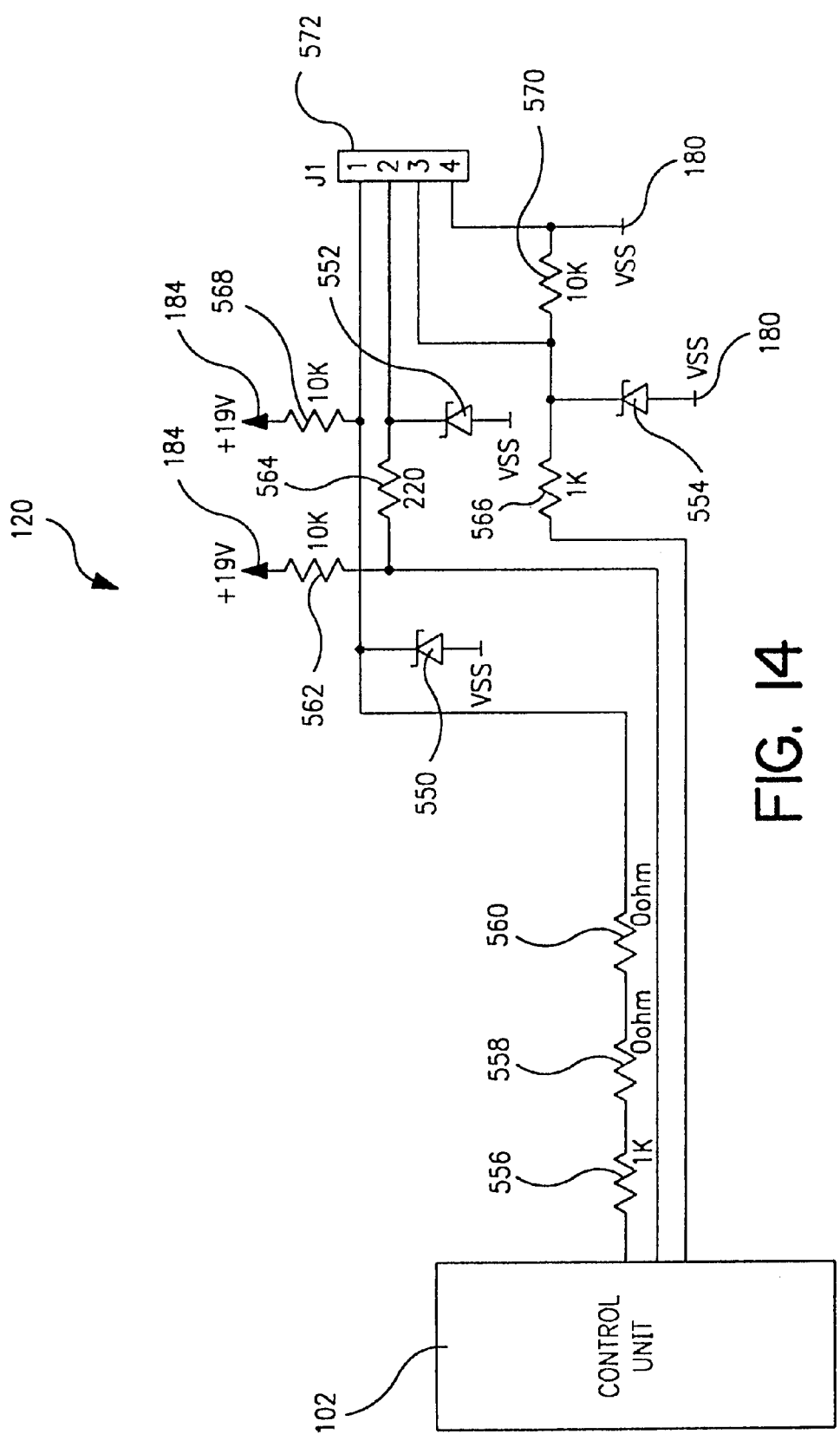
FIG. 14 is an electrical circuit schematic of the communication port.

Referring to FIG. 14, as previously set forth, the communications port 120 is connected with the control unit 102. The communications port 120 is used by the control unit 102 to communicate bidirectionally with a peripheral device (not shown), such as a personal computer or a hand-held device. In the preferred embodiment, the communications port 120 comprises a plurality of zenar diodes 550, 552, 554 and a plurality of resistors 556, 558, 560, 562, 562, 566, 568, 570, which are electrically connected as illustrated in FIG. 14. The first DC power source 180 and the second DC power source 184 provide power to the communications port 120. The communications port 120 is designed to use the RS-232 communications standard, as well known in the art. A port connector 572 is provided so that the peripheral device can be connected with the communications port 120. Those skilled in the art would recognize that different types of communication ports may be used and are beyond the scope of the present invention. To that end, the preferred communications port 120 disclosed herein is by way of example only and should not be construed as a limitation of the present invention.

While the invention has been described in its currently best known modes of operation and embodiments, other modes and embodiments of the invention will be apparent to those skilled in the art and are contemplated. In addition, although the preferred embodiment of the present invention is directed to a water treatment system 10, those skilled in the art would recognize that the present invention may be readily incorporated in several different types of fluid treatment systems.

What is claimed is:

1. A fluid treatment system with a radio frequency identification system, comprising:
   a control unit positioned in a fluid treatment system housing;
   a replaceable electromagnetic radiation emitting assembly positioned in said fluid treatment system housing;
   a base station located in said fluid treatment system housing and electrically connected to a coil and said control unit, wherein said coil is capable of transmitting and receiving radio signals in response to a predetermined set of control signals from said base station; and
   a radio frequency identification transponder positioned in said electromagnetic radiation emitting assembly that is in radio communication with said base station.

2. The fluid treatment system of claim 1, wherein said radio frequency identification transponder includes a responder antenna and a read/write chip.

3. The fluid treatment system of claim 1, wherein said radio frequency identification transponder is capable of transmitting an electromagnetic radiation emitting device serial number to said base station for use by said control unit.

4. The fluid treatment system of claim 1, wherein said radio frequency identification transponder is capable of transmitting an electromagnetic radiation emitting device start limit to said base station for use by said control unit.

5. The fluid treatment system of claim 1, wherein said radio frequency identification transponder is capable of transmitting an electromagnetic radiation emitting device on-time limit to said base station for use by said control unit.

6. The fluid treatment system of claim 1, wherein said radio frequency identification transponder is capable of transmitting an electromagnetic radiation emitting device install time limit to said base station for use by said control unit.

7. The fluid treatment system of claim 1, wherein said radio frequency identification transponder is capable of transmitting an electromagnetic radiation emitting device cycle on-time to said base station for use by said control unit.

8. The fluid treatment system of claim 1, wherein said radio frequency identification transponder is capable of transmitting a cycle mode low temperature to said base station for use by said control unit.

9. The fluid treatment system of claim 1, wherein said radio frequency identification transponder is capable of transmitting a minimum electromagnetic radiation emitting device on time to said base station for use by said control unit.

10. The fluid treatment system of claim 1, wherein said radio frequency identification transponder is capable of transmitting an electromagnetic radiation emitting device high-mode time to said base station for use by said control unit.

11. The fluid treatment system of claim 1, wherein said radio frequency identification transponder is capable of transmitting an electromagnetic radiation emitting device preheat time to said base station for use by said control unit.

12. The fluid treatment system of claim 1, wherein said radio frequency identification transponder allows said control unit to keep track of electromagnetic radiation emitting device install time.

13. The fluid treatment system of claim 1, wherein said radio frequency identification transponder allows said control unit to keep track of electromagnetic radiation emitting device powered time.

14. The fluid treatment system of claim 1, wherein said radio frequency identification transponder allows said control unit to keep track of electromagnetic radiation emitting device starts.

15. The fluid treatment system of claim 1, wherein said radio frequency identification transponder allows said control unit to keep track of electromagnetic radiation emitting device cold starts.

16. A fluid treatment system with a radio frequency identification system, comprising:
   a control unit positioned in a fluid treatment system housing;
   a replaceable filter assembly positioned in said fluid treatment system housing;
   a base station positioned in said fluid treatment system housing and electrically connected to a coil and said control unit, wherein said coil is capable of transmitting and receiving radio signals in response to a predetermined set of control signals from said base station; and
   a radio frequency identification transponder positioned in said filter assembly that is in radio communication with said base station.

17. The fluid treatment system of claim 16, wherein said radio frequency identification transponder includes a responder antenna and a read/write chip.

18. The fluid treatment system of claim 16, wherein said radio frequency identification transponder is capable of transmitting a filter unit serial number to said base station for use by said control unit.

19. The fluid treatment system of claim 16, wherein said radio frequency identification transponder is capable of transmitting a filter assembly volume limit to said base station for use by said control unit.

20. The fluid treatment system of claim 16, wherein said radio frequency identification transponder is capable of transmitting a filter assembly install time limit to said base station for use by said control unit.

21. The fluid treatment system of claim 16, wherein said radio frequency identification transponder is capable of transmitting a plugged filter threshold percentage to said base station for use by said control unit.

22. The fluid treatment system of claim 16, wherein said radio frequency identification transponder allows said control unit to keep track the filter assembly install time.

23. A method of monitoring electromagnetic radiation emitting assembly information in a fluid treatment system, comprising the steps of:

providing a replaceable electromagnetic radiation emitting assembly for use in said fluid treatment system;

generating an electromagnetic radiation emitting assembly information signal with an electromagnetic radiation emitting identification transponder located in said replaceable electromagnetic radiation emitting assembly;

transmitting said electromagnetic radiation emitting assembly information signal to a coil connected to a base station in said fluid treatment system; and directing said electromagnetic radiation emitting assembly information signal to a control unit.

24. The method of claim 23, wherein said electromagnetic radiation emitting assembly includes an ultraviolet lamp.

25. The method of claim 23, wherein said electromagnetic radiation emitting assembly includes a pulsed white light lamp.

26. The method of claim 23, wherein said electromagnetic radiation emitting device is a dielectric barrier discharge lamp.

27. The method of claim 23, wherein said electromagnetic radiation emitting radio frequency identification transponder includes a responder antenna and a read/write chip.

28. The method of claim 23, wherein said electromagnetic radiation emitting assembly information signal contains an electromagnetic radiation emitting device serial number.

29. The method of claim 23, wherein said electromagnetic radiation emitting assembly information signal contains an electromagnetic radiation emitting assembly start limit.

30. The method of claim 23, wherein said electromagnetic radiation emitting assembly information signal contains an electromagnetic radiation emitting on-time limit.

31. The method of claim 23, wherein said electromagnetic radiation emitting assembly information signal contains an electromagnetic radiation emitting assembly install time limit.

32. The method of claim 23, wherein said electromagnetic radiation emitting assembly information signal contains an electromagnetic radiation emitting assembly cycle on-time.

33. The method of claim 23, wherein said electromagnetic radiation emitting assembly information signal contains a cycle mode low temperature.

34. The method of claim 23, wherein said electromagnetic radiation emitting assembly information signal contains a minimum electromagnetic radiation emitting assembly on time.

35. The method of claim 23, wherein said electromagnetic radiation emitting assembly information signal contains an electromagnetic radiation emitting assembly high-mode time.

36. The method of claim 23, wherein said electromagnetic radiation emitting assembly information signal contains an electromagnetic radiation emitting assembly preheat time.

37. The method of claim 23, wherein said electromagnetic radiation emitting radio frequency identification transponder allows said control unit to keep track of electromagnetic radiation emitting assembly install time.

38. The method of claim 23, wherein said electromagnetic radiation emitting radio frequency identification transponder allows said control unit to keep track of electromagnetic radiation emitting assembly powered time.

39. The method of claim 23, wherein said radio frequency identification transponder allows said control unit to keep track of electromagnetic radiation emitting assembly starts.

40. The method of claim 23, wherein said radio frequency identification transponder allows said control unit to keep track of electromagnetic radiation emitting assembly cold starts.

41. A method of monitoring filter assembly information in a fluid treatment system, comprising the steps of:

providing a replaceable filter assembly for use in said fluid treatment system;

generating a filter assembly information signal with a filter assembly radio frequency identification transponder located in said replaceable filter assembly;

transmitting said filter assembly information signal to a coil connected to a base station located in said fluid treatment system; and directing said filter assembly information signal to a control unit.

42. The method of claim 41, wherein said filter assembly information signal contains a filter unit serial number.

43. The method of claim 41, wherein said filter assembly information signal contains a filter assembly volume limit.

44. The method of claim 41, wherein said filter assembly information signal contains a filter assembly install time limit.

45. The method of claim 41, wherein said filter assembly information signal contains a plugged filter threshold percentage.

46. The method of claim 41, wherein said filter assembly radio frequency identification transponder allows said control unit to keep track the filter assembly install time.

47. A fluid treatment system with a radio frequency identification system, comprising:

a control unit positioned in a fluid treatment system housing;

a replaceable electromagnetic radiation emitting assembly positioned in said fluid treatment system housing;

a base station located in said fluid treatment system housing and electrically connected to said control unit, wherein said base station is capable of transmitting and receiving radio signals in response to a predetermined set of control signals from said control unit; and a radio frequency identification transponder positioned in said electromagnetic radiation emitting assembly that is in radio communication with said base station.

48. A fluid treatment system with a radio frequency identification system, comprising:

a control unit positioned in a fluid treatment system housing;

a replaceable filter assembly positioned in said fluid treatment system housing;

a base station positioned in said fluid treatment system housing and electrically connected to said control unit, wherein said base station is capable of transmitting and receiving radio signals in response to a predetermined set of control signals from said control unit; and a radio frequency identification transponder positioned in said filter assembly that is in radio communication with said base station.

* * * * *